United States Patent [19]

Virtanen et al.

[11] Patent Number: 5,834,473

[45] Date of Patent: Nov. 10, 1998

[54] METHOD FOR TREATING COCCIDIOSIS

[75] Inventors: Erkki Virtanen, Helsinki; Mika Koivistoinen, Hirvihaara, both of Finland; James L. McNaughton, Easton, Md.; Liisa Rosi, Nummela, Finland

[73] Assignee: Cultor, Ltd., Helsinki, Finland

[21] Appl. No.: 903,186

[22] Filed: Jun. 5, 1997

Related U.S. Application Data

[63] Continuation of Ser. No. 389,821, Feb. 15, 1995, abandoned, which is a continuation-in-part of Ser. No. 202,112, Feb. 25, 1994, abandoned, which is a continuation-in-part of Ser. No. 53,138, Apr. 29, 1993, abandoned.

[51] Int. Cl.$^6$ .................. A61K 31/505; A61K 31/35; A61K 31/205
[52] U.S. Cl. ................... 514/259; 514/460; 514/556
[58] Field of Search ................... 514/259, 460, 514/556

[56] References Cited

U.S. PATENT DOCUMENTS

| | | | |
|---|---|---|---|
| 3,959,519 | 5/1976 | Johnson | 426/648 |
| 4,218,438 | 8/1980 | Callender et al. | 424/115 |
| 4,857,555 | 8/1989 | Smith et al. | 514/563 |
| 4,861,758 | 8/1989 | Raether | 514/27 |
| 5,063,219 | 11/1991 | Schildknecht et al. | 514/157 |
| 5,141,925 | 8/1992 | Alroy et al. | 514/23 |
| 5,182,299 | 1/1993 | Gullans et al. | 514/460 |
| 5,183,687 | 2/1993 | Hunter | 424/78.34 |
| 5,314,700 | 5/1994 | Barnes et al. | 424/684 |
| 5,397,803 | 3/1995 | Smith et al. | 514/563 |
| 5,516,798 | 5/1996 | Ferket | 514/556 |

FOREIGN PATENT DOCUMENTS

| | | |
|---|---|---|
| 0 182 117 A1 | 5/1986 | European Pat. Off. . |
| 291705 | 1/1971 | U.S.S.R. . |
| WO 94/24886 | 11/1994 | WIPO . |

OTHER PUBLICATIONS

Gwyther, M.J. and Britton, W.M., "The influence of coccidial infections and ionophore treatment of tissue cations and anions in broiler chicks," *Coccidia and Intestinal Coccidiomorphs*, Vth International Conf., Tours, France, pp. 279–284 (Oct. 17–20, 1989) INRA Publ. (Les Colloques de l'INRA, No. 49).

Hafez, Y. S. M. et al., "Methionine Toxicity in Chicks and Poults," *Poultry Science* 57:699–703 (1978).

Harper, H.A., in: Review of Physiological Chemistry, Appleton & Lange, Publ., Los Altos, CA, pp. 120 and 351 (1973).

Harter, J.M. and Baker, D.H., "Factors Affecting Methionine Toxicity and Its Alleviation in the Chick," *J. Nutr.* 108:1061–1070 (1978).

McCue, K.F. and Hanson, A.D., "Drought and Salt Tolerance: Towards Understanding and Application," *Trends in Biotechnology* 8:358–362 (1990).

McNaughton J.L., "Effect of Betaine on the Potentiation of an Ionophore Coccidiostat (BIO–COX) in the Control of Coccidiosis for Growing Broiler Chickens," *Summary Report by Finnsugar Bioproducts*, Letter and Data sent to distributors in Mar. 1993, 7 pages.

Nash, D. et al., "Effects of Proline, Betaine and some other Solutes on the Heat Stability of Mitochondrial Enzymes," *Aust. J. Plant Physiol.* 9:47–57 (1982).

Nutrient Requirements of Poultry, Eighth Revised Edition, National Research Council, pp. 4–5 (1984).

Nutrient Requirements of Poultry, Ninth Revised Edition, National Research Council, pp. 27–28 (Mar., 1994).

Papageorgiou G.C. et al., "On the Mechanism of Betaine Protection of Photosynthetic Structures in High Salt Environment," *Curr. Res. In Photosynthesis I*:957–960 (1990) Kluwer Academic Publishers (Netherlands).

Patrick, H. et al., in: Poultry: Feeds & Nutrition, Second Edition, AVI Publishing Co. Inc., Westport, CT, Chapters 36–38, pp. 417–480 (1980).

Pesti, G.M. et al., "Sulfur Amino Acid and Methyl Donor Status of Corn–Soy Diets Fed to Starting Broiler Chicks and Turkey Poults," *Poultry Science* 58:1541–1547 (1979).

Rudolph, A.S. et al., "Effects of Three Stabilizing Agents—Proline, Betaine, and Trehalose—on Membrane Phospholipids," *Archives Biochem. Biophys*, 245(1):134–143 (1986).

Ruff, M.D., "Reasons for Inadequate Nutrition Utilization During Avian Coccidiosis: A Review," *Georgia Coccidiosis Conference*, pp. 169–183 (Nov. 19–21, 1986).

Scott M. et al., in: Nutrition of the Chicken, Second Edition, M.L. Scott & Associates, Ithaca, N.Y., pp. 104 and 469 (1976).

Speight, D., "Inter–relationship between ionophore coccidiostats and nutrients in poultry feeds," *6th European Symposium on Poultry Nutrition, World's Poultry Science Association*, Konigslutter, Germany, D23–D34 (Oct. 11–15, 1987).

Stekol, J.A. et al., "Labile Methyl Group and Its Synthesis De Novo in Relation to Growth in Chicks," *J. Biol. Chem.* 203:763–773 (1953).

Titus, H. et al., in: The Scientific Feeding of Chicken, Fifth Edition, The Interstate Publishers, Danville, IL, pp. 230–233 (1971).

Yancey, P.H. et al., "Living with Water Stress: Evolution of Osmolyte Systems," *Science* 217: 1214–1222 (1982).

Almquist, H.J. and Grau, C.R., "Growth–Promoting Activity of Betaine in the Chick," *J. Biol. Chem.* 149:575–576 (1943).

(List continued on next page.)

Primary Examiner—Kimberly Jordan
Attorney, Agent, or Firm—Sterne, Kessler, Goldstein & Fox P.L.L.C.

[57] ABSTRACT

The invention is directed to methods for the treatment of coccidiosis and compositions designed to be administered to animals infected with coccidiosis-inducing organism. The compositions contain an osmoprotectant, and especially, betaine.

18 Claims, 4 Drawing Sheets

OTHER PUBLICATIONS

Almquist, H.J. and Grau, C.R., "Interrelation of Methionine, Choline, Betaine and Arsenocholine in the Chick," *J. Nutrition* 27:263–269 (1944).

Ferket, P.R., "Flushing may be related to growth rate in turkeys," *Turkey World*, pp. 10–11 (Apr.–May 1994).

Ilan, Y. et al., "Gastrointestinal involvement in homocystinuria," *J. Gastroenterol. Hepatol.* 8:60–62 (Jan.–Feb. 1993).

Lien, Y–H.H. et al., "Characterization of organic osmolytes in avian renal medulla: a nonurea osmotic gradient system," *Am. J. Physiol.* 264(6):R1045–R1049 (Jun. 1993).

McGinnis, J. et al., "Effect of Ethanolamine and Betaine on Perosis in Chicks," *Proc. Soc. Exp. Biol. Med.* 51:293–294 (1942).

Moeckel, G.W. and Lein, Y–H.H., "Bicarbonate dependency of betaine synthesis in cultured LLC–$PK_1$ cells," *Am. J. Physiol.* 266:F512–F515 (Mar. 1994).

Listing of Legere Pharmaceutical Products, esp. Prevenzyne®, and Betaine HCl, *Physician's Desk Reference*, 41st Edition, Huff, B.B., Ed., Edward R. Barnhart, and the Medical Economics Company Inc., Pub., Oradell, New Jersey, pp. 1122–1123, (1987).

Saunderson, C.L. and Mackinlay, J., "Changes in body-weight, composition and hepatic enzyme activities in response to dietary methionine, betaine and choline levels in growing chicks," *Br. J. Nutrition* 63:339–349 (1990).

Virtanen, E. et al., "Effects of Food Containing Betaine/Amino Acid Additive on the Osmotic Adaptation of Young Atlantic Salmon, *Salmo salar* L.," *Aquaculture* 83:109–122 (1989).

Zypan Tablets, Standard Process Laboratories, Inc., *Physican's Desk Reference*, 41st Edition, Huff, B.B., Ed., Edward R. Barnhart, and the Medical Economics Company Inc., Pub., Oradell, New Jersey, p. 1972 (1987).

McNaughton, J.L., Study Report, "Effect of Betaine on the Potentiation of Bio–Cox in the Control of Coccidisis [sic] for Growing Broiler Chickens and Comparison with Effect of Methionine" (Apr. 30, 1994).

Quarles, C.L., Final Report, Project PA–93–B1, "Effects of Betaine on Reduction of Coccidiosis When Fed With Bio–Cox to Male Broiler Chickens" (Apr. 30, 1994).

Quarles, C.L., Summary Report, "Effects of Betaine on Broiler Performance and Carcass Quality When Given a Mild Infection of Coccidiosis" (Apr. 30, 1994).

Quarles, C.L., Final Report, Project No. PA–93–2, "Effects of Betaine on Broiler Performance and Carcass Quality When Given a Mild Infection of Coccidiosis" (Apr. 30, 1994).

Quarles, C.L., Final Report, Project No. PA–93–3, "Effect of Betaine on Ascites and Sudden Death Syndrome in Broilers" (Apr. 30, 1994).

Quarles, C.L., Final Report, Project PA–93–4, "Comparison of the Effects of Betaine on Broiler Performance and Carcass Quality when Birds are Grown with or without an Experimentally Induced Coccidiosis Infection" (Apr. 30, 1994).

McNaughton, J.L., Trail 93–FIN–04–B Battery Study, "Efficacy of Betaine in Improving Nutrient Utilization in Broiler Chicks 1–21 Days of Age During Coccidiosis" (Apr. 30, 1994).

McNaughton, J.L., Trail 93–FIN–04–B Battery Study, "Efficacy of Betaine in Improving Nutrient Utilization in Broiler Chicks 1–21 Days of Age During Coccidiosis" Report Revised Mar. 1994 (Apr. 30, 1994).

McNaughton, J.L., Trail 94–FIN–08–B, "Efficacy of Betaine in Improving Growing Broiler Performance and Processing Characteristics Fed Various Coccidiostats" (May 30,1994).

Virtanen, E., "Betaine for Weaning and Scouring," 7 pages (Apr. 30, 1994).

Schwartz, L.D., "Perosis (Slipped Tendon)," *Poultry Health Handbook*, 2nd Edition, College of Agriculture, The Pennsylvania State University, University Park, PA, p. 167 (1977).

BETAFIN–Natural Betaine, Finnsugar Bioproducts Infoletter (1991 or later).

English translation of the non–English language portion of Quarles, C.L., Final Report, Project No. PA–93–2, "Effects of Betaine on Broiler Perfomance and Carcass Quality When Given a Mild Infection of Coccidiosis," total of 4 pages (Jun. 1993).

*Merck Veterinary Manual: A Handbook of Diagnosis, Therapy, and Disease Prevention and Control for the Veterinarian*, Fraser, C.M. et al., eds., Merck & Co., Inc., Rathway, N.J., pub., pp. 1256–1259; and 1560–1563 (1986).

McNaughton, J.L., "Biological Availability of Betaine for the Placement of Methionine for Growing Broiler Chickens" (Jun. 30, 1992).

Baker, D.H., "Amino Acid Interactions with Vitamins, Minerals, and Drugs," In: *Handbook, 1984 Nutrition Institute on Amino Acids*, National Feed Ingredients Association, West Des Moines, Iowa pp. 1–9 (1984).

Baker, D.H. and Czarnecki, G.L., "Transmethylation of Homocysteine to Methionine: Efficiency in the Rat and Chick," *J. Nutr.* 115:1291–1299 (1985).

Gilka, J. et al., "Amino Acid Composition of Meat, Fatty Acid Composition of Fat and Content of Some Chemical Elements in the Tissues of Male Lambs Fed Monensin or Lasalocid," *Meat Sci.* 25:273–280 (1989).

Myers, D., "Organic Chemistry of Surfactants," In: *Surfactant Science and Technology*, VCH Publishers, Inc., New York, N.Y., pub., pp. 73–78 (1988).

Quarles, C.L., Summary Report, "Effects of Betaine on Broiler Performance and Carcass Quality When Given a Mild Infection of Coccidiosis" (Sep. 1993).

Tsiagbe, V.K. et al., "Enhanced Immune Responses in Broiler Chicks Fed Methionine–Supplemented Diets," *Poultry Sci.* 66:1147–1154 (1987).

McNaughton, J.L., Study Report, "Effect of Betaine on the Potentiation of Bio–Cox in the Control of Coccidisis [sic] for Growing Broiler Chickens and Comparison with Effect of Methoionine," Study Conducted Aug. 25–Oct. 9, 1992.

Quarles, C.L., Final Report, Project PA–93–B1, "Effects of Betaine on Reduction of Coccidiosis When Fed With Bio–Cox to Male Broiler Chickens," Mar. 11, 1993.

Quarles, C.L., Summary Report, "Effects of Betaine on Broiler Performance and Carcass Quality When Given a Mild Infection of Coccidiosis," Jul. 5, 1993.

Quarles, C.L., Final Report, Project No. PA–93–2, "Effects of Betaine on Broiler Performance and Carcass Quality When Given a Mild Infection of Coccidiosis," Jun. 21, 1993.

Quarles, C.L., Final Report, Project No. PA–93–3, Effect of Betaine on Ascites and Sudden Death Syndrome in Broilers, Jun. 4, 1993.

Quarles, C.L., Final Report, Project PA–93–4, Comparison of the Effects of Betaine on Broiler Performance and Carcass Quailty when Birds are Grown with or without an Experimentally Induced Coccidiosis Infection, Oct. 1993.

McNaughton, J.L., Trail 93–FIN–04 B Battery Study, "Efficacy of Betaine in Improving Nutrient Utilization in Broiler Chicks 1–21 Days of Age Coccidiosis," Study Conducted Aug.17–Sep. 7, 1993.

McNaughton, J.L., Trail 93–FIN–04–B Battery Study, "Efficacy of Betaine in Improving Nutrient Utilization in Broiler Chicks 1–21 Days of Age During Coccidiosis," (Report Revised Mar. 1994).

McNaughton, J.L., Trail 94–FIN–08–B, "Efficacy of Betaine in Improving Growing Broiler Performance and Processing Characteristics Fed Various Coccidiostates," Trail Dates Apr. 26–May 17, 1994.

Virtanen, E., "Betaine for Weaning and Scouring," Study Conducted 1993, 7 pages.

METHOD FOR TREATING COCCIDIOSIS

BACKGROUND OF THE INVENTION

Cross Reference to Related Applications

This application is a continuation of application Ser. No. 08/389,821, filed Feb. 15, 1995, now abandoned, which is a continuation-in-part of U.S. application Ser. No. 08/202,112, filed Feb. 25, 1994, now abandoned, which is a continuation-in-part of U.S. application Ser. No. 08/053,138, filed Apr. 29, 1993, now abandoned; the contents of each are hereby incorporated by reference.

1. Field of the Invention

This invention relates to methods for treating coccidiosis in animals, by administering efficacious levels of an osmoprotectant, and especially, betaine, with or without coccidiostat. The methods of the invention are also useful for the treatment of clinical or subclinical coccidiosis symptoms, including such symptoms that arise after vaccination against the disease.

2. Background of the Invention

Loses due to parasitic diseases are among the chief causes of economic loss to the livestock and poultry industry. The availability of antiparasitic treatments has enabled the development of higher levels of livestock and poultry production. Efficient and economic antiparasitic treatments also facilitate a worldwide supply of relatively cheap protein. Effective parasite prevention and control is especially important in the poultry industry, where the positive economic impact of antiparasitic prophylaxis, treatment and therapy is significant.

Coccidiosis is a common disease in domestic food animals, caused by protozoa belonging to the Eimeria family. Coccidiosis is found worldwide, and its economical impact, particularly on poultry farming, is huge. In the U.S. poultry industry alone, coccidiosis causes losses of 200–250 million dollars yearly. World-wide, coccidiosis is estimated to cause one third of all disease and mortality losses in the poultry industry (*Trends in Veterinary Research and Development*, part 6, Anti-coccidials, Lloyd-Evans, L. P. M. (ed.), PJB Publications Ltd., 1991).

Animals harboring coccidiosis infections may manifest severe or mild clinical symptoms or they may be entirely subclinical. The site of infection, i.e., tissue tropism, depends on the species of the parasite and the host. The majority of Eimeria and Isospora species infect the animal's intestinal epithelium. Severe infections are characterized by diarrhea, dehydration, emaciation and death. Mild and subclinical infections may manifest no overt clinical symptoms, but nevertheless the animals may suffer depressed growth, impaired feed conversion, loss of skin pigmentation and downgrading of the animal's assessed quality in terms of fitness for human consumption.

In chickens, typical clinical signs of coccidiosis include ill-thrift (lack of thriving), rapid loss of weight, diarrhea, and dysentery. The most serious effects take place in the intestine, where coccidia invade the mucosae and cause epithelial damage, lesions and hemorrhage. Physiologically, coccidiosis causes severe disturbances in the acid-base, ionic and osmotic balance of the gut, and decreases nutrient absorption (Ruff, Georgia Coccidiosis Conference, Nov. 19–21 (1986) pp. 169–183; Gwyther et al., *Coccidia and Intestinal Coccidiomorphs*, Vth International Conf., Oct. 17–20 (1989) pp. 279–284).

Since the 1950s, several dietary drugs (coccidiostats) have been developed to treat coccidiosis, but with only moderate success. The most serious drawbacks associated with the use of coccidiostats have been: 1) rapidly developing resistance of the parasites; 2) adverse effects on host animals; and 3) risk for residuals or quality defects in the consumer products. While the universal use of coccidiostats has decreased serious mortality outbreaks, subclinical effects of coccidiosis on animals markedly decrease productivity (Jeng & Edgar, *Highlights of Agricultural Research—Alabama*, Agricultural Experiment Station, v.28, p.6 (1981)). Therefore, compositions and methods for decreasing the use of coccidiostats or increasing their efficacy are needed.

Many coccidiostats in common use kill parasites by breaking down their ionic and osmotic regulation. However, these drugs are not coccidia specific; they also alter the ionic and osmotic balance of the host and, consequently, may decrease nutrient absorption in the gut (Speight, 6th European Symposium on Poultry Nutrition, World's Poultry Science Assoc., Oct. 11–15 (1987), abstract 7A). As a result, the positive effect of coccidiostats on mortality may be offset by their detrimental side effects with regard to nutrient availability, growth and feed efficiency. Methods for protecting the animals against the detrimental side effects of the ionophoric coccidiostats are also needed.

Vaccination of animals has become an alternative, if not the preferred method for the treatment and prevention of parasitic diseases in animals. However, vaccination is not free of side effects. The most serious drawback of the vaccines, is that they tend to reduce the growth and feed efficiency of the animal's because the vaccine deliberately induces mild symptoms of the disease in the animal. This effect may last for a few weeks after the vaccine has been introduced. These side-effects negatively impact on the vaccinated animal's performance and thus also have an adverse economic impact.

Vaccines, especially, attenuated live vaccines are useful in the poultry industry for the inoculation of birds against coccidiosis. Live vaccines are also used, but are mostly limited to breeder flocks. Live vaccines are not considered suitable for broiler production because of the potential accumulation of live parasites in the litter.

In the use of vaccines against Eimeria parasites in poultry, the use of attenuated live anticoccidial vaccines has been limited to layers (egg-laying hens) and broilers that are grown to heavier weights. The use of these vaccines has been limited to chickens with longer growing periods because only these chickens have sufficient time to recover from the ill side-effects of the vaccine and thus are able to compensate for the vaccine-induced loss in growth. Therefore, methods for eliminating the side-effects of vaccination with coccidiosis vaccines are needed.

Betaine is an osmoprotectant. It increases the osmotic strength of cells without adversely affecting enzyme activity, and it protects enzymes from ionic or temperature inactivation (Nash et al., *Aust. J. Plant Physiol.* 9:47–57 (1982); Yancey et al., *Science* 224:1064–1069 (1982); Rudolph et al., *Archives Biochem. Biophys.* 245:134–143 (1986); McCue & Hanson, *Trends in Biotechnology* 8:358–362 (1990); Papageorgiou et al., *Curr. Res. In Photosynthesis* 1:957–960 (1990)). While some organisms (and tissues) can accumulate betaine in high quantities under osmotic stress through osmotically induced betaine synthesis, most animals lack this capability, and are dependent upon the intake of exogenous betaine. For example, isolated salmon liver mitochondria, when exposed to osmotic stress, show increased betaine intake, but not synthesis (Björköy, G., Synthesis and Accumulation of glycine betaine in Salmon (*Salmo salar*) and a Mussel, MSc thesis, Norwegian College of Fisheries, University of Tromsö, pp. 94).

Betaine has mainly been studied for its ability to act as a methyl donor in transmethylation reactions (Stekol et al., *J. Biol. Chem.* 203:763–773 (1953)) and for its ability to transfer methyl groups to homocysteine to produce methionine (Harper, in *Review of Physiol. Chem.*, 120 and 351 (1973)). Although betaine's chemical osmoprotective properties were known prior to the present invention, it was not appreciated that betaine or other osmoprotectants might be useful, in vivo, in alleviating the undesirable side effects associated with coccidiosis infection. In addition, it was not previously recognized that osmoprotectants, and especially betaine, plus a coccidiostat can act favorably together, even synergistically, to improve the commercial performance of domestic food animals suffering from coccidiosis.

SUMMARY OF THE INVENTION

Recognizing the problems that arise in current methods for treating animals for coccidiosis infection, and cognizant of the need for improvement in the same, the inventors investigated compositions and methods for improving the commercial performance of domestic food animals suffering from coccidiosis. These studies have culminated in the discovery of compositions and methods that effectively and economically counter the symptoms of coccidiosis infections. These studies have also culminated in the discovery of compositions and methods for enhancing the efficacy of coccidiostats, especially ionophoric coccidiostats.

Therefore, the invention is directed to compositions and methods for treating coccidiosis and thus improving the commercial performance of domestic food animals by administration of an osmoprotectant, and especially, betaine in the diet of such animal; these compositions and method are applicable whether such infections were deliberately induced by vaccination, or whether such infections were environmentally transmitted through contagious infection from the animal's surroundings.

In a further embodiment of the composition and method for treating coccidiosis, an osmoprotectant, and especially betaine, and a coccidiostat are administered.

In a further embodiment, the invention is directed to a feed for animals, especially domestic food animals, such feed containing an osmoprotectant, and especially betaine at levels sufficient for the efficacious treatment of coccidiosis infections in the animal that consumes such feed.

BRIEF DESCRIPTION OF THE FIGURES

FIG. 1 shows the percent mortality for chicks grown for 45 days on unsupplemented diets, diets supplemented with 44 ppm of salinomycin, and or on diets with 66 ppm salinomycin. The effect of each diet was examined both with and without added betaine. It can be seen that betaine addition reduced chick mortality for each of the diets studied.

FIG. 3 shows the end weights of chicks grown for 45 days on each of the three different types of diets described above. In each case, supplementation with betaine resulted in chicks with an increased end weight.

FIG. 6 shows the effect of betaine addition on the mortality of coccidia-infected chicks. At a dose of 0.75 kg/metric ton, betaine reduced the mortality of chicks fed diets containing either a low or an adequate amount of methionine.

FIG. 7 shows that betaine increases the end weight of coccidia-infected chicks in diets which are both low in methionine or which contain adequate methionine FIG. 8 shows that betaine improves feed conversion ratio in chicks infected with coccidia regardless of whether the chicks are grown on feed low in methionine or with adequate methionine.

DESCRIPTION OF THE PREFERRED EMBODIMENTS

A. Definitions

Figure 1:
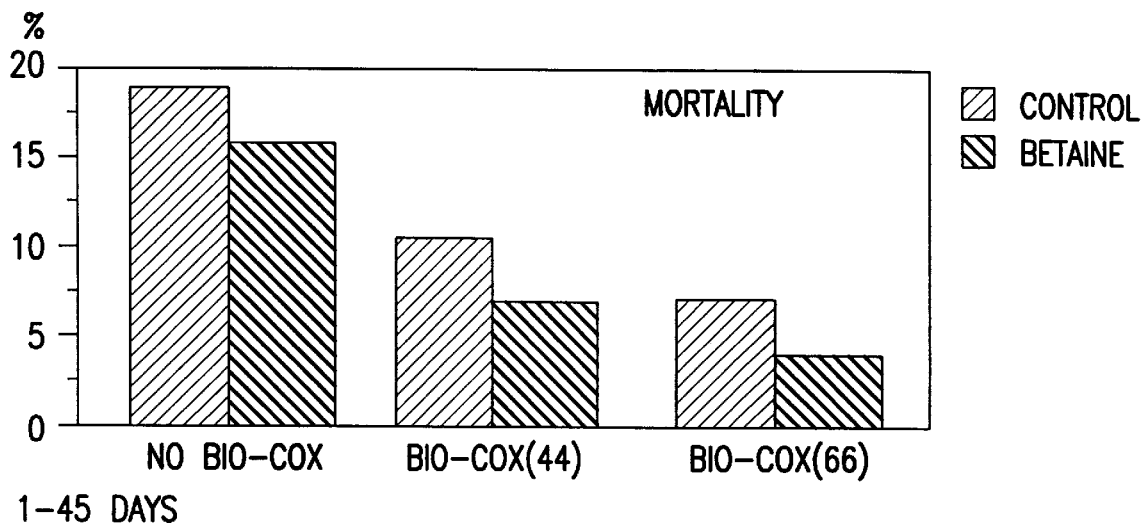
FIG. 1.
Figure 2:
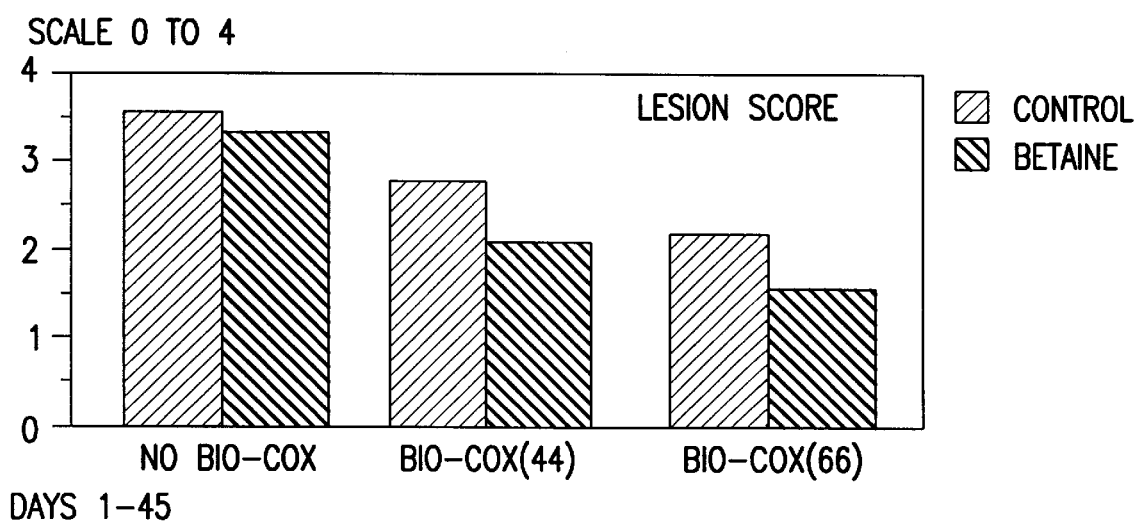
FIG. 2: Chicks grown for 45 days on unsupplemented feeds or on feeds supplemented with 44 ppm coccidiostat and 66 ppm coccidiostat were necropsied and the severity of gut lesions (Johnson and Reid, *Exp. Parasitol* 28:30–36 (1970), see description of the method at pages 11–12 of this application) ranked on a scale of 0 to 4. It can be seen that, in all cases, supplementation of diets with betaine led to a reduced severity of gut lesions.
Figure 3:
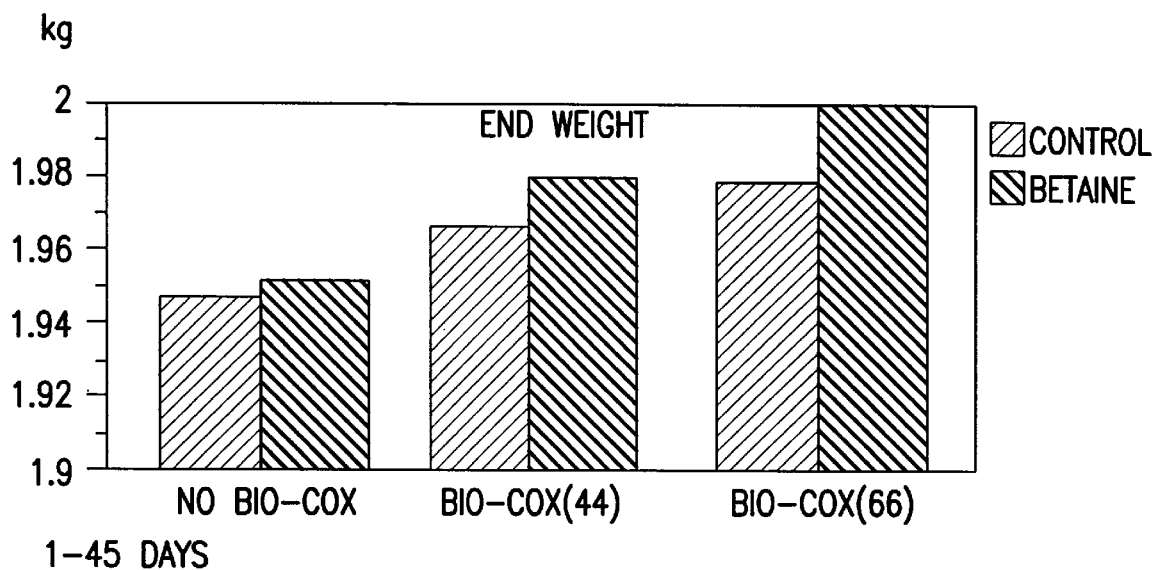
FIG. 3.
Figure 4:
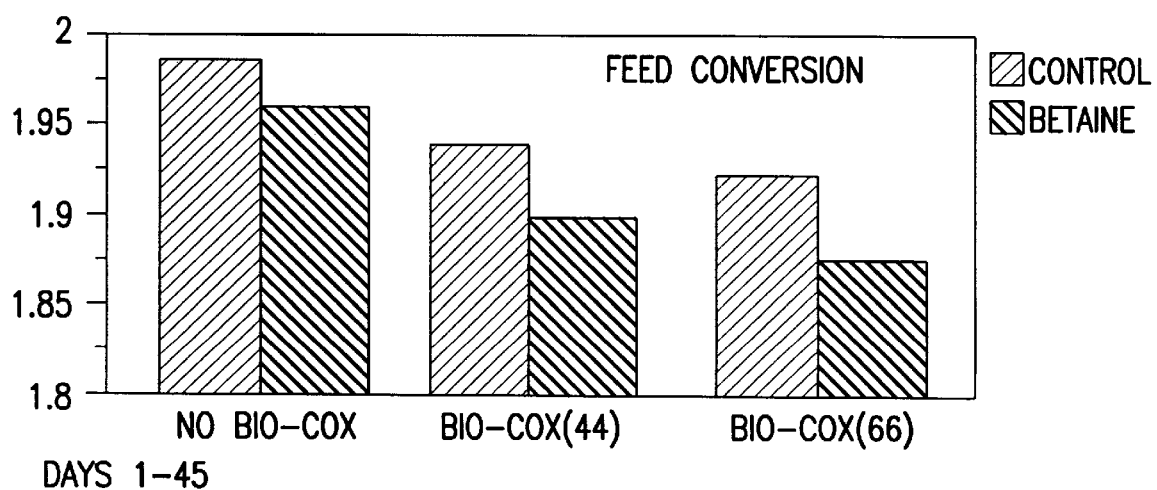
FIG. 4: The feed conversion ratio of chickens grown on each of the three different types of diets was determined and the results are shown in FIG. 4. In each instance, betaine resulted in chicks with improved efficiencies.

"Adverse effects" are those physiological effects that are undesired but the direct result of some action, such as the administration of a vaccine; examples of adverse effects in the case of attenuated Coccidia vaccines include the symptoms of coccidiosis, including a reduction of feed efficiency, reduction in growth efficiency, and the appearance of intestinal lesions.

An "attenuated" organism refers to a selected strain of a virulent organism that does not cause clinical symptoms associated with the parent (wild type) organism, but is still capable of sufficient replication to induce gut lesions and immunity in a desired host.

A "basal diet" is the diet fed to chicks prior to supplementation with either methionine or betaine.

"Betaine," also called "glycine betaine," is defined chemically as 1-carboxy-N,N,N-trimethylmethanaminium hydroxide inner salt. Betaine is sold by Finnsugar Bioproducts under the tradename of "Betafin."

"Carcass composition" or "carcass quality" refer to the relative size of the various edible parts or cuts of an animal and the ratio of fat to protein in the animal carcass. For example, a chicken carcass composed of a high percentage of breast meat and a low percentage of fat would have a desirable carcass composition and would be a high quality carcass.

"Chemical coccidiostats" are all anti-coccidial agents that are not ionophore coccidiostats.

"Chill weight" is the carcass weight after chilling.

"Coccidiostat" refers to a drug used in the treatment of an infection caused by an organism of the Order Coccidia.

"Commercial performance," as used herein, refers to the extent to which animals raised under a specific set of conditions are commercially desirable as food animals. For the purposes of this invention, there are four parameters that determine commercial performance: mortality; end weight; feed conversion efficiency; and carcass composition or quality. An improvement in any one of these parameters results in an improved commercial performance provided that the remaining parameters are not changed in a manner that is unacceptable, and, preferably, either remain unchanged or also improve.

"Corn-soy feed" is feed mainly comprised of yellow corn, soybean meal and soy oil.

"Co-treatment" means the administration of a composition to an animal concurrent with or after the first administration of a vaccination. The administration of the composition may continue for the entire life of the animal after the initial administration of the vaccine.

A "domestic food animal," for the purposes of the present invention, is any domestic animal that is consumed as a source of protein in the diet of humans or other animals. Typical domestic animals include: bovine animals (e.g. cattle); ovine animals (e.g. sheep); swine (e.g. pigs); fowl (e.g. chickens and turkeys); rabbit and the like.

An "efficacious level" of a substance is an amount that is sufficient to immunize, prevent, ameleorate, cure or otherwise effectively protect against or treat a certain pathological or infectious disease state, such as, for example, coccidiosis.

"Feed conversion efficiency" is the ratio of the amount of weight gained by an animal divided by the amount of feed consumed by the animal. For example, a feed with an efficiency of 1.0 would mean that for every kilogram of feed consumed, the animal gained 1.0 kilogram. The feed conversion efficiency includes the weight of animals that died during the experiment.

"Feed conversion ratio" is the ratio of the amount of feed consumed by an animal divided by the amount of weight gained by the animal. The feed conversion ratio includes the weight of animals that died during the experiment.

"Feedstuffs" are defined as those commonly used ingredients such as, for example, yellow corn or soybean meal, which are combined to formulate the diet of an animal.

A "finisher diet" is the diet fed to chickens 40 to 49 days of age (week 7–8).

A "grower diet" is the diet fed to chickens 21 to 40 days of age (week 4–6).

"Hot weight" is carcass weight immediately after evisceration.

"Ionophore coccidiostats" are anti-coccidial agents which, by virtue of their molecular shape and structure, can act as ion transporters across biological membranes.

"Mortality" is defined as the number of chicks within a treatment group that die during the course of an experiment. Typically mortality is expressed as a percentage and determined by dividing the number of chicks that die by the total number of chicks at the start of the experiment and then multiplying by 100.

"Poultry" means any animal fowl including, for example, chickens, turkeys, ducks, geese, quail, pigeons, and guinea fowl.

"Precocious strain oocyte" means oocyte strains selected with a shortened prepatent period.

A "premix" refers to a composition of two or more components that have been combined for a particular use in diluted less-concentrated form. For example, a composition containing homogeneously blended osmoprotectant, and especially betaine, with a coccidiostat is a pre-mix that can be added to chicken feed to produce a feed having a desired final osmoprotectant/coccidiostat concentration without the necessity of adding them separately.

"Pretreatment" means the administration of a composition to an animal before, i.e. in anticipation of, the administration of a second, later treatment, such as a vaccination. The pretreatment composition may be continually administered for the entire life of the animal after administration of the vaccine. "This is the same as a dietary additive."

"Probiotics" means seeding the gut with desirable organisms for the purposes of competitive exclusion of unwanted bacteria such as Salmonella, pathogenic $E.$ $coli,$ Listeria, Campylobacter, and other pathogens.

"Significant," as used herein, means statistically significant. Thus, a statement that "treated chicks had significantly reduced mortality relative to untreated chicks" means that $P<0.05$ using standard statistical analyses.

A "starter diet" is the diet fed to chickens during the first 21 days of life (week 0–3).

"Subclinical" refers to an early stage in the evolution of a disease, and especially a disease state wherein a disease is present without manifest symptoms.

"Ton" when used with a metric measurement, such as a kilogram, is the metric ton (for example: kg/metric ton); "ton" when used with a non-metric measurement, is the "short" ton (for example, lb/ton).

"Vaccination" refers to the administration of a composition that contains an antigenic agent that, when administered to an animal, stimulates the immune system of an animal to respond, preferably to the specific active agent. The response may be humoral or cellular. The immune stimulation may be prophylactic, therapeutic or anamnestic.

"Vaccine" refers to the administered composition that is to be administered in a vaccination. Vaccines contain the active agent, i.e. the antigen, and may also contain preservatives, carriers or adjuvants (such as mineral oils).

B. Detailed Description

In the following description, reference will be made to various methodologies known to those skilled in the art of veterinary immunology and immunopathology, vaccines, animal pharmacy and animal husbandry. Publications and other materials setting forth such known methodologies to which reference of made are incorporated herein by reference in their entireties as though set forth in full.

General principles of veterinary science are set forth, for example, in *The Merck Veterinary Manual,* 6th Edition, edited by Fraser et al., 1986; the Food and Drug Administration's FDA 1994 *Feed Additive Compendium,* U.S. Food and Drug Administration, 1994; *Trends in Veterinary Research and Development,* part 6, Anti-coccidials, edited by Lloyd-Evans, L. P. M., PJB Publications Ltd., 1991; *Diseases of Poultry,* edited by B. W. Calnek, Iowa State University Press, Ames, Iowa, 1991.

General principles of animal husbandry are set forth, for example, in H. Patrick et al., *Poultry: Feeds & Nutrition,* Second Edition, AVI Publishing Co. Inc., Westport, Conn. (1980).

General principles of pharmaceutical sciences are set forth, for example, in *Remington's Pharmaceutical Sciences* (18th edition, A. R. Gennaro, ed., Mack Publishing, Easton, Pa. 1990).

"Coccidiosis" is a generic name applied to a disease caused by parasitic protozoa of the Phylum Apicomplexa, Order Coccidia. The Order Coccidia includes the genera Eimeria, Isospora, Toxoplasma, Sarcocystis, and Besnoitia. Coccidiosis is usually limited to diseases of the digestive tract caused by pathogenic species within the genera Eimeria and Isospora. "Eimeria" defines protozoa of the genus Eimeria, Phylum Apicomplexa, Order Coccidia. Coccidiosis is usually limited to diseases of the digestive tract caused by pathogenic species within the genera Eimeria and Isospora.

In the genus Eimeria, oocytes undergo sporulation forming sporoblasts which eventually become sporocytes containing sporozoites (the infective stage of Coccidia). The oocyst is passed in the feces of the infected animal. When eaten, the oocyte wall breaks, the sporocysts are released and the sporozoites emerge as "excysted sporozoites." Each sporulated oocyst has four sporocysts, each sporocyst has two sporozoites. Excystation may occur naturally or through ex vivo manipulation for the purposes of vaccination. An "excysted sporozoite" is the live sporozoite that emerges from the protective shell of the sporocyst.

Animals infected with Coccidia generally fail to thrive. They lose weight, inefficiently utilize feed, and seem depressed, often quietly huddling together. The severity of coccidiosis can be evaluated by the severity of the animal's gut lesions. The severity of coccidiosis-induced gut lesions are generally evaluated by the method of Johnson and Reid, Exp. Parasitol 28:30–36 (1970). In this method, the lesion is scored on a scale of 0–4. A score of "0" indicates no gross lesion. A score of "+1" indicates very few scattered petechiae on the intestinal wall; no thickening of the intestinal walls; normal intestinal contents present. A score of "+2" indicates lesions more numerous with noticeable blood in the intestinal contents; intestinal wall is somewhat thickened; normal intestinal contents present. A score of "+3" indicates a large amount of intestinal blood or intestinal cores present; intestinal walls greatly thickened; little if any fecal contents in the intestine. A score of "+4" indicates intestinal walls greatly distended with blood or large caseous cores; fecal debris lacking or included in the cores; dead birds are scored as +4. A mild coccidiosis disease is deliberately induced in animals when they are vaccinated with coccidiosis vaccines. The physiological effects of the infecting Coccidia used in the vaccines are the same, but without the severity of an environmentally-transmitted infection. All the lesion score values given express the sum of lesion scores at four different measuring points of the intestine (upper, middle, lower, cecal).

The present invention is directed to a composition and method of treating animals infected with coccidiosis, whether such infection was deliberate (through vaccination) or environmental (through undesired contagious transmission from the animal's surrounding), by administration of a composition containing efficacious levels of an osmoprotectant, betaine in the most preferred embodiment, in the diet of such animal. When desired, an osmoprotectant, and especially betaine, may be administered together with efficacious levels (amounts useful for innoculation against coccidiosis or for treatment of coccidiosis, depending upon the desired use) of a coccidiostat. In an embodiment of the compositions and methods of the invention, an osmoprotectant and a coccidiostat act favorably together, even synergistically, to improve the commercial performance of domestic food animals suffering from coccidiosis.

The compositions and methods of the invention are useful for the treatment of any animal, including domestic food animals, pets, zoo animals, and the like, including, for example, poultry, cattle, rabbits, goats, swine, sheep, dogs, cats, birds and fish. A preferred embodiment of the invention is directed to an embodiment wherein the animals are vaccinated poultry, including but are not limited to, chickens, geese, guinea fowl, pigeons, ducks, quail, and turkeys.

The administration of (1) an osmoprotectant, and especially betaine, or, the administration of (2) an osmoproctectant, and especially betaine, with a coccidiostat, has been found to be especially effective at reducing the mortality and improving the overall performance of animals infected with Coccidia. The data presented herein establish, for the first time, that osmoprotectants and especially betaine can offset the commercially detrimental effects caused by Coccidia parasites. In addition, a treatment that includes both an osmoprotectant such as betaine and a coccidiostat may be used; the beneficial effect of such osmoprotectant occurs whether the coccidiostat is of either the chemical or ionophore type.

Examples of osmoprotectants include inorganic ions (such as potassium ion, sodium ion, lithium ion, magnesium ion, calcium ion and manganese ion); amino acids (such as proline, glycine, methionine, glutamine, glutaminic acid, alanine, asparaginic acid, asparagine, valine, threonine, isoleucine, taurine, and lycine); methylated amines-amino acids and their derivatives (such as betaine, creatine, choline, carnitine, taurine-betaine, β-alanine-betaine, γ-butyro-betaine, choline choride, choline sulphate, choline-inositol, choline esters, and phenyl propanolamine); sugars and sugar alcohols (such as sorbitol, mannitol, inositol, pinitol, trehalose, erytritol, mannosucrose, raffinose, glycerol, stachyose, fructo oligosaccharides) and other organic molecules (such as abscisic acid, urea, stachydrine, ectoine, hydroxyectoine, pipecholic acid, and usnic acid).

As shown herein, administration of an osmoprotectant as recited above, and especially administration of betaine, either alone, or in combination with a coccidiostat to animals that are at risk for, or diagnosed with, coccidiosis, significantly diminished the severity of gut lesions and reduced mortality. For food animals, there was also an improvement in higher end weights and improved feed conversion efficiency. Such improved performance is herein said to be a "treatment" for coccidiosis infections, whether such infections were deliberate due to vaccination or were environmentally transmitted. Thus, the invention is directed to a compositions and method for reducing the mortality and/or improving growth and feed efficiency of animals suffering from acute or subclinical symptoms associated with coccidiosis.

According to the invention, efficacious levels of an osmoprotectant, and especially betaine, may be administered to alleviate the adverse effects of any coccidiosis-inducing pathogen, and especially, any Eimeria species including for example, the Eimeria species necatrix, galloparvonis, meleagrimitis, innocua, meleagridis, subrotunda, dispersa, truncata, acervulina, brunetti, maxima, mitis, praecox and tenella.

According to the invention, efficacious levels of an osmoprotectant, and especially betaine, may be administered to alleviate the adverse effects in poultry due to infection by Eimeria species, especially, the Eimeria species *E. acervulina, E. brunetti, E. maxima, E. mitis, E. necatrix, E. praecox* and *E. tenella*.

According to the invention, efficacious levels of an osmoprotectant, and especially betaine, may be administered to alleviate the adverse effects induced in cattle when infected with a member of the Eimeria species, especially, the Eimeria species zuernii, bovis (smithii), ellipsoidlis.

According to the invention, efficacious levels of an osmoprotectant, and especially betaine, may be administered to alleviate the adverse effects induced in sheep when infected with a member of the Eimeria species including the Eimeria species arloingi A (ovina), weybridgensis (arlongis B), crandallis, ahsata, ovinoidalis, gilruthi.

According to the invention, efficacious levels of an osmoprotectant, and especially betaine, may be administered to alleviate the adverse effects induced in goats when infected with a member of the Eimeria species including, for example, immunization with the Eimeria species arloingi, faurei, caproina, ninakohlyakimovae, christenseni.

According to the invention, efficacious levels of an osmoprotectant, and especially betaine, may be administered to alleviate the adverse effects induced in pigs when infected with a member of the Eimeria species including, for example, immunization with the Eimeria species debliecki, scabra, penninuta; and, including adverse effects induced by a member of the Isospora species, for example, *Isospora suis*.

Example 1 describes experiments in which chicks were inoculated with coccidia and then fed diets supplemented with an osmoprotectant (exemplified with betaine), coccidiostat (exemplified with salinomycin) or a combination of osmoprotectant and coccidiostat. Chicks raised on the supplemented diets were compared with inoculated chicks fed unsupplemented diets and with chicks not inoculated with coccidia. Chicks fed a diet containing a combination of betaine and coccidiostat for 21 days had significantly higher body weights and significantly fewer gut lesions than chicks fed a diet containing an equivalent concentration of either betaine or salinomycin alone.

In that example, although neither betaine alone nor coccidiostat alone were able to completely offset the effects of the Coccidia infection on feed conversion efficiency, when administered together, they produced an efficiency which was comparable to that of the noninoculated controls. Mortality in 21 day old chicks fed diets containing 44 ppm of salinomycin was significantly reduced relative to the mortality of infected chicks fed either an unsupplemented diet or a diet supplemented with betaine alone. When betaine and 44 ppm coccidiostat were used together, mortality was reduced to a level which was not significantly higher than the mortality of the noninoculated chicks.

It may also be seen from Table 5 that, at 45 days, chicks receiving feed containing both an osmoprotectant (exemplified by betaine) and a coccidiostat had a mortality significantly lower than chicks receiving feed with only one of the agents and that the mortality of the chicks administered both agents was reduced to the point where it was no longer significantly higher than that of the noninoculated controls. Similarly, the body weight and feed conversion ratio of chicks on diets with betaine and 66 pm of coccidiostat were not significantly different from the control group, whereas chicks receiving only one of the agents had significantly lower body weights and a significantly higher feed conversion efficiency.

The results shown in Example 2 indicate that the positive effects of osmoprotectant and coccidiostat on the commercial performance of chicks infected with coccidia do not depend upon the methionine content of the diet. Thus, the anti-coccidial effect of the osmoprotectant (exemplified by betaine) is independent of its ability to substitute for methionine. The results suggest that the protective effect of the osmoprotectant is probably related to its ability to offset the detrimental effects of coccidiosis on nutrient absorption. Supporting this hypothesis is the finding that infected chicks fed diets with an osmoprotectant (exemplified by betaine) have less severe gut lesions than chickens fed either unsupplemented diets or diets supplemented with coccidiostat alone (Table 5).

Example 3 demonstrates that the synergistic improvement in commercial performance evidenced by the combination of osmoprotectant (exemplified by betaine) and salinomycin is maintained both with other types of ionophore coccidiostats (lasalocid) as well as with chemical coccidiostats (halofuginone hydrobromide). As shown in Table 13, the combination of lasalocid and betaine produced chicks with significantly higher body weights and significantly lower feed conversion ratios compared to chicks receiving diets supplemented with either betaine or lasalocid alone. Chicks receiving the combination of halofuginone hydrobromide and betaine evidenced a significantly reduced feed conversion ratio. In addition, the results shown in Table 13 confirm the conclusion that the combination of salinomycin and betaine improves commercial performance. Chicks receiving salinomycin together with betaine exhibited significantly increased body weights and improved feed conversion ratios relative to chicks receiving either salinomycin or betaine alone.

Example 4 provides examples of additional coccidiostats, and demonstrates the wide range of effectiveness of the osmoprotectant (exemplified by betaine) co-administration. Example 5 extends these results to other animals.

Example 6 demonstrates the osmoprotectant's (exemplified by betaine) effectiveness at improving commercial performance characteristics in chicks vaccinated against coccidiosis—and in which a mild coccidiosis infection generally develops. Example 7 extends these results to other animals.

The data presented herein establish, for the first time, that coccidiostat efficacy is increased in the presence of an osmoprotectant such as betaine, and that osmoprotectants such as betaine and coccidiostats can act together, even synergistically, and never in a counterproductive manner, to offset the detrimental effects, especially the commercially important detrimental effects on growth rates, caused by Coccidia parasites. Synergism between the action of osmoprotectants, exemplified by betaine, and the coccidiostat can occur with a coccidiostat of either the chemical or ionophore type.

The enhancing effects of the osmoprotectants, and especially betaine, are best revealed when a coccidiostat is not completely effective, which is common in commercial animal farming. Because of the synergistic effect of osmoprotectants, and especially betaine, the concentration of coccidiostat that it is necessary to administer to animals to obtain commercially acceptable results can be lowered. This is exemplified in Example 1 for salinomycin, wherein, when provided with efficacious amounts of an osmoprotectant, a final concentration of salinomycin of 44 ppm has been found to be efficacious, even though 66 ppm is the recommended dose. Thus, the use of betaine in combination with coccidiostat may reduce the cost of formulating an acceptable feed by reducing the amount of the costly coccidiostat, and thus also reduce the exposure of consumers to any low residual levels of coccidiostat in the animal.

In the composition and methods of the invention, the osmoprotectant, and especially betaine is preferably added to the diet of an animal, especially an animal infected with a coccidiosis-causing organism, at a concentration of between 0.1 kg per metric ton and 5.0 kg per metric ton of dry feed. In a preferred embodiment, betaine is added to the animal's diet at a concentration of between 0.5 kg per metric ton and 2.0 kg per metric ton dry feed. In a highly preferred embodiment, betaine is added to the animal's diet at a concentration of 1.5 kg per metric ton dry feed. The osmoprotectant, and especially betaine may also be provided in the animal's water supply. In another preferred embodiment, the osmoprotectant, and especially betaine, is administered at the concentration of 0.01 to 0.5 g per kg body weight of the animal. In another preferred embodiment, betaine is administered at the concentration of 0.03 to 3.0 kg per metric ton of drinking water.

It has been found that administration of osmoprotectants, and especially betaine, to vaccinated animals reduces or eliminates the symptoms of coccidiosis that are the result of the vaccination. Accordingly, in one embodiment of the invention, efficacious amounts of osmoprotectants, and especially betaine, equivalent to those amounts recited above, are provided to an animal that will be, or has been vaccinated against coccidiosis. Any desired vaccine may be used in this embodiment as it is the induction of a mild case of the coccidiosis disease that is brought about by the vaccine that is the site of betaine action.

In a preferred embodiment, the desired animal, preferably poultry, and most preferably, chicks, is vaccinated with an vaccine efficacious in inducing or otherwise providing immunological protection against one or more strains of pathogens that cause coccidiosis; the animal then placed on a diet that contains efficacious amounts of the osmoprotectant, and especially betaine, so as to ameliorate or eliminate the symptoms of the disease. The vaccination may be with an attenuated live parasite, killed parasites, genetically engineered antigens, surface protein fragments, live oocytes, attenuated precocious strain oocytes or suspensions of live excysted sporozoites.

In one embodiment, animals are administered betaine after vaccination against coccidiosis causing protozoa, especially protozoa belonging to the Order Coccidia, with a preferred embodiment directed to compositions and methods for alleviating the adverse effects of vaccination of animals against the genus Eimeria. In a preferred embodiment the betaine is administered after vaccination against the anticoccidial vaccines Coccivac-B™, Coccivac-D™, Coccivac-T™, Immucox™ and Paracox™. Especially preferred are those vaccines that provide protection against more than one species of Eimeria. For example, Paracox is a stabilized suspension of attenuated lines of seven species of Eimeria (E. acervulina, E. brunetti, E. maxima, E. mitis, E. necatrix, E. praecox and E. tenella.

The desired animals can be vaccinated as young as possible, using methods known in the art. Chickens are preferably vaccinated at one day of age. Examples of useful live vaccines include Immunocox (Lee, E.-H., Can. Vet. J. 28:434–436 (1987)), Coccivac (Sterwin Laboratories), and that described in U.S. Pat. No. 5,068,104. Examples of useful attenuated, live vaccines include Paracox (Pitman-Moore Limited).

The osmoprotectant-containing diet, and especially, the betaine-containing diet, may be given prior to vaccination with no detrimental effect on the host. However, the osmoprotectant-containing diet, and especially, the betaine-containing diet, should also be given after vaccination as its beneficial effects are best seen when administered during the infection period, preferably on a daily basis, and most preferably for at least 1–2 weeks after vaccination. The osmoprotectant-containing diet may be provided throughout the life of the animal.

Preferably, the vaccine is administered in a manner suitable for mass application, such as a coarse particle spray onto the animals, or mixed into the drinking water. Alternatively, eyedrop vaccination (by dropping the liquid vaccine directly onto the conjunctival tissue of the eye) or injection can be performed. When the vaccine is provided at 1 day of age, according to the invention, betaine is also provided in the food at 1 day of age, and continuously until slaughter. Useful sites of delivery of the vaccine in the methods of the invention include intrabursal inoculation, intracoelomic inoculation (Ragland et al., U.S. Pat. No. 5,004,607), intranasal inoculation and intratracheal inoculation.

The administration of the osmoprotectant-containing composition, and especially the administration of a betaine-containing composition, can be independent of the animal's diet and provided by any other efficacious means. Accordingly, and especially for non-vaccinated animals, osmoprotectant, and especially betaine, is administered with a coccidiostat.

When it is desired to administer the osmoprotectant, and especially betaine, with a coccidiostat (a drug useful for the treatment of coccidiosis), any useful anticoccidial agent may be used in the composition and method of the invention. Coccidiostats (and the approved USA level for poultry in parentheses) include amprolium (0.0125–0.025%); amprolium (0.0125%) with ethopabate (0.0004–0.004%); arsanilic acid or sodium arsanilate (0.04%); buquinolate (0.00825%), chlortetracycline (0.022%), clopidol or meticlorpindol (0.0125–0.025%); decoquinate (0.003%); dibutyltin dilaurate (butynorate (0.0375% for turkeys); dinitolmide (zoalene) (0.004–0.0125%); furzaolidone (0.0055–0.011 %); lasalocid (0.0075–0.0125%); monensin (0.01–0.0121 %); nicarbazin (0.0125%); nitrofurazone (0.0055%); nitromide (0.025% with sulfanitran (0.03%) and with roxarsone (0.005%); oxytetracycline (0.022%); robenidine (0.0033%); salinomycin (0.004–0.0066%); sulfadimethoxine (0.0125% with ormetoprim (0.0075%); sulfaquinoxaline (0.015%–0.025%). In "parts per million" (ppm), typical recommended inclusion rates for chick diets are: monensin: 100–120 ppm; salinomycin: 60 ppm; narasin: 70 ppm; and lasalocid: 90 ppm. In the case of salinomycin, a final concentration of between 44 and 66 ppm has been found to be efficacious (see Example 1). Preferred ionophore coccidiostats are salinomycin and lasalocid.

Useful chemical coccidiostats include nitro-carbanalide (nicarbazin); quinolone (decoquinate); pyridon, guanidine (robenidine, robenide hydrochloride); quinazoline (halofuginone; thiamine antagonist (amprolium); toluamide (zoalene); potentiated sulfa (sulfadimethoxine with ormetoprim; and ionophone with carbanilide (narasin with nicarbazin). The preferred chemical coccidiostat is halofuginone hydrobromide. Examples of useful coccidiostats and preferred animal species are shown in Table 1.

TABLE 1

Coccidiostats and FDA Approved Target Animals

| Drug | Animal Species |
| --- | --- |
| Amprolium | CH, LH, TU, PH, CF |
| Clopidol | CH, TU |
| Decoquinate | CH, CT, GO |
| Halofugionone hydrobromide | CH, TU |
| Lasalocid | CH, CT, SH |
| Maduramicin ammonium | CH |
| Monensin | CH, TU, CT, QU, GO |
| Narasin | CH |
| Nicarbazin | CH |
| Robenide hydrochloride | CH |
| Salinomycin | CH (SW outside USA) |
| Zoalene | CH, TU |

CH = chick,
LH = laying hen,
TU = turkey,
PH = pheasant,
CF = calf,
CT = cattle,
GO = goat,
SH = sheep,
QU = quail,
SW = swine Coccidiostats by themselves are very seldom 100% effective due to the resistance of different Eimeria spp. Coccidiostats, when administered by themselves, do not generally have the same efficacy against all members of the Eimeria spp. However, according to the invention, it is possible to enhance the efficacy of the coccidiostats and protect the animals against the results of such infection by the administration of a combination of osmoprotectant, and especially betaine, and coccidiostat.

The coccidiostat may be administered in the animal's osmoprotectant-containing water, and especially the animal's betaine-containing water, or in the animal's osmoprotectant-containing feed, and especially, a betaine-containing feed. For example, amprolium, pyrimethamine with sulfaquinoxaline, nitrofurazone (soluble), sodium sulfachloropyrazine monohydrate, sulfadimethoxine and sulfamethazine (sulfadimidine) can be given in the animal's drinking water. Alternatively, the osmoprotectant, and especially betaine, may be provided in the feed and the coccidiostat in the drinking water, or vice verse.

Useful concentrations of coccidiostat for species other than chickens are found in the FDA 1994 Feed Additive Compendium, U.S. Food and Drug Administration, 1994. In addition, the recommended usage should be followed, withdrawing the coccidiostat the recommended days before slaughter, if necessary.

The present invention includes feeds for animals, preferably poultry and most preferably chickens, that are formulated to contain osmoprotectant, and especially betaine, and, if desired, a coccidiostat. In order to prepare such feeds, a basal diet is first formulated using any of a variety of that animal's routine feedstuffs such as corn, soy, wheat and barley (see *AFMA Feed Ingredient Guide,* published by the American Feed Manufacturer's Association, Arlington, Va., U.S.A.; H. Patrick et al., *Poultry: Feeds & Nutrition,* Second Edition, AVI Publishing Co. Inc., Westport, Conn., chapter 37, (1980)). All mixing and other preparation of feeds takes place using routine procedures well-known in the art (see e.g., H. Patrick et al., *Poultry: Feeds & Nutrition,* Second Edition, AVI Publishing Co. Inc., Westport, Conn., chapters 36–38 (1980); *Feed Manufacturing Technology,* H. Pfost and C. Swinehart eds., American Feed Manufacturer's Association Inc., Chicago, Ill., (1970)).

The nutrient content of the basal diet may be determined using standard feedstuff analysis tables. For poultry, such tables are provided in, e.g., H. Patrick et al., *Poultry: Feeds & Nutrition,* Second Edition, AVI Publishing Co. Inc., Westport, Conn., pp. 438–449 (1980); H. Titus et al., *The Scientific Feeding of Chickens,* Fifth Edition, The Interstate Publishers, Danville, Ill., chapter 13 (1971)). Vitamins, minerals and other nutrients may be added to concentrations determined by turning to various available references (see e.g., *Nutrient Requirements of Poultry,* National Research Council, National Academy of Sciences, Washington, D.C. (1984)).

A standard diet for other animal may be formulated using the information provided by the Merck Veterinary Manual, sixth edition, pages 1104–1132 (1986). Using the same source, standard diets can be prepared for rabbits (pages 1210–12110); sheep (1211–1221); swine (pages 1221–1230); and poultry (pages 1188–1210). After the basal diet has been formulated, coccidiostat and osmoprotectant, and especially betaine, are added. The concentration of coccidiostat should be that recommended by the Food and Drug Administration (FDA 1994 Feed Additive Compendium, U.S. Food and Drug Administration, 1994).

Once the basal diet has been formulated, efficacious levels of the desired osmoprotectant, and especially betaine, and, if desired, coccidiostat are added. These agents may either be added individually, or they may be added together as a premix. A premixes of osmoprotectant, and especially betaine, and coccidiostat is especially useful for the treatment of pets and zoo animals, since the appropriate amount of the premix can be conveniently blended into the individual food for that animal, or which the animal prefers.

In addition to being directed to feeds containing both an osmoprotectant, and especially betaine, and coccidiostat, the present invention encompasses other physical forms that may be provided that contain these two agents which are administered to animals for the purpose of preventing the adverse effects of coccidiosis. A premix of osmoprotectant and especially betaine, and coccidiostat may be administered either in the form of powder, pellets, tablets, capsules or liquids. In all cases the concentration of osmoprotectant, and especially betaine, and coccidiostat should result in a dietary inclusion rate comparable to that for feeds formulated to contain these agents. The osmoprotectant/coccidiostat composition and especially the betaine/coccidiostat composition may be supplemented with additives to improve its flavor or to provide other dietary supplements or therapeutic agents needed by animals. Such administration is especially desirable for those animals in which mixture into the animal's food is not possible, or the animal is too sick to eat the necessary amount.

Compounds containing the desired osmoprotectant, and especially betaine, and, if desired, coccidiostat for parenteral administration can be formulated according to known methods for preparing pharmaceutically useful compositions in which these agents are combined in admixture with a pharmaceutically acceptable carrier vehicle. Suitable vehicles and their formulation are described, for example, in *Remington's Pharmaceutical Sciences* (16th edition, A. Oslow, ed., Mack, Easton, Pa. 1980). The required dosage will depend upon the type of animal being treated and the type of coccidiostat being administered (FDA 1994 Feed Additive Compendium, U.S. Food and Drug Administration, 1994).

Additional pharmaceutical methods may be employed to control the duration of action. Controlled delivery may be accomplished by selecting appropriate macromolecules such as polyesters, polyaminoacids, polypyrrolidone, ethylene vinylacetate, methylcellulose, carboxymethyl-cellulose or protamine sulfate and combining these according to well-established procedures in order to control release. The duration of action of coccidiostat and the osmoprotectant, and especially betaine, may also be controlled by incorporating these agents into particles of polymeric materials such polyesters, polyaminoacids, hydrogels, poly (lactic acid) or ethylene vinylacetate copolymers. Alternatively, it may be possible to entrap the osmoprotectant and especially betaine and coccidiostat in microcapsules. Various materials and methods for making and using microcapsules are disclosed in *Remington's Pharmaceutical Sciences,* (16th edition, A. Oslow, ed., Mack, Easton, Pa. 1980).

In addition to the embodiment of the invention wherein the method for administering osmoprotectant and especially betaine to animals is in the form of the animal's dietary feed, the present invention further embodies the use of other compositions containing osmoprotectant, and especially betaine, i.e. the osmoprotectant, and especially betaine, may be co-administered with any desired composition, including any vaccines, nutrients or medicaments. Examples of useful medicaments include glycoproteins, antibiotics, antiparasitics, antivirals, probiotics, growth stimulators and sexual function modifiers. Examples of useful antibiotics include tetracyclines, spectinomycin, cephalosporin, gentamicin, lincomycin and quinolones. Examples of useful nutrient additives include vitamins, minerals, amino acids, sugars and fatty acids. Examples of useful glycoproteins include those as described for the treatment of coccidiosis in animals in Alroy et al., U.S. Pat. No. 5,141,925. Examples of useful growth stimulators include growth hormone, growth hormone releasing hormone, insulin-like growth factors I and II, interleukins, nerve growth factors, thyroxine stimulating hormone, thyroxine and corticosterone. Examples of sexual function modifiers include medullarin inhibitory substance, 17-beta-estradiol, estrone, estrogen, progesterone, testosterone, epiandrostenedione, gonadotropin releasing hormone, follicle stimulating hormone, luteinizing hormone and prolactin.

While exemplified herein for the treatment of coccidiosis, it is contemplated that the methods and compositions of the invention would be useful for the treatment of any disease in which the osmotic properties of a host animal were challenged by infection of a pathogen or other event. That is, it is expected that the administration of an osmoprotectant, and especially betaine, with or without a drug that is specific for treatment of, or immunity against, a certain pathogen, will be generally efficacious for the treatment of any infection or condition in which the osmotic system of the host, especially the intestinal environment, is abnormal and in need of protection.

The osmoprotectant, and especially betaine, may be administered to alleviate adverse effects in animals infected with any internal or external parasite (endo- and ectoparasites), including, for example, protozoa (as coccidiosis), worms (as tapeworms, heartworms, roundworms), liver flukes, ticks and tick-borne diseases (as Lyme disease), grubs (as cattle grubs), flies (blowflies, buffalo flies), viruses, bacteria, fungi and yeast.

The osmoprotectant, and especially betaine, may be administered to alleviate adverse effects in poultry infected with Newcastle disease; infectious bronchitis; infectious bursal disease; herpes virus (including Marek's disease virus, Gallid herpesvirus 1, infectious laryngotracheitis virus (ILTV)); avian reovirus; infectious laryngotracheitis; avian encephalomyelitis; avipoxvirus coccidiosis; fowl cholera; mycoplasma including live *Mycoplasma gallisepticum* (MG); fowl cholera including *Pasteurella multocida;* Avipoxvirus, including avian pox viruses as fowlpox, turkey pox, quail pox, pigeon pox, canary pox; bordetellosis including *Bordetella avium;* infectious coryza including *Haemophilus paragallinarum.*

The osmoprotectant, and especially betaine, may be administered to counter the effect of live or attenuated live vaccines, which may include additional genetically engineered antigen-producing capabilities, include but are not limited to vaccines against the herpes virus, including Marek's disease virus, Gallid herpesvirus 1 (infectious laryngotracheitis virus (ILTV)); reovirus; Newcastle disease (ND) including $B_1$ ND virus, lentogenic ND, viscerotropic velogenic ND, neurotropic velogenic ND, or mesogenic ND; infectious bronchitis virus (IBV); infectious bursal disease virus (IBDV); avian encephalomyelitis virus (AEV) (Picorniviidae); mycoplasma including live *Mycoplasma gallisepticum* (MG); fowl cholera including *Pasteurella multocida;* Avipoxvirus, including avian pox viruses as fowlpox, turkey pox, quail pox, pigeon pox, canary pox; bordetellosis including *Bordetella avium;* infectious coryza including *Haemophilus paragallinarum.* All of these may also be administered in an inactivated form.

All citations herein are incorporated by reference in their entirety. Having now described the invention in general terms, the same will be further described by reference to a specific example provided herein for the purpose of explanation only and not intended to be limiting unless otherwise specified.

EXAMPLE 1

Animals: 2,464 one-day-old male and 2,464 one-day-old female broiler chicks of commercial strain (Peterson x Arbor Acres) were randomly allotted to 56 floor pens on built-up litter. Chicks were grown to 45 days of age. There were seven treatment groups, each with eight replicates. The experimental design is shown in Table 4.

Inoculation: Chicks in treatments 1 to 6 were inoculated at 14 days of age with a mixture of *E. acervulina, E. maxima* and *E. tenella* via drinking water. At 21 days of age, two males and two females from each pen were necropsied and scored for coccidiosis (0–4, 4 is most severe). Treatment 7 was a non-inoculated control, but chicks received a natural contaminant via the litter.

Diets: Corn-soy diets (starter and grower) were formulated to meet or exceed the nutritional requirements set forth in *Nutrient Requirements of Poultry,* National Research Council, National Academy of Sciences, Washington, D.C. (1984). Diet composition is shown in Table 2 and calculated analysis in Table 3. The diets were supplemented with betaine and the coccidiostat salinomycin, according to the experimental design (Table 4). Diets were supplied in crumble and pellet form ad libitum. A complete record of feed consumption was maintained.

The results are disclosed in the following tables and figures. The letters after the numerical data indicate the statistical significance of the differences between the treatments, determined with analysis of variance. Treatments marked with the same letter do not differ significantly as regards the measured parameter.

TABLE 2

| DIET COMPOSITION | | |
|---|---|---|
| Ingredient | Starter (%) | Grower (%) |
| Yellow corn | 60.88 | 65.88 |
| Soybean meal (48) | 32.15 | 27.26 |
| Fat | 4.01 | 4.06 |
| Salt | 0.29 | 0.27 |
| L-Lysine-HCl | 0.14 | 0.06 |
| DL Methionine | 0.15 | 0.15 |
| Limestone | 0.69 | 0.91 |
| Def. phos | 1.71 | 1.47 |
| Trace mineral premix | 0.05 | 0.05 |
| Vitamin premix | 0.05 | 0.05 |
| Bacitracin MD | 0.05 | 0.05 |

TABLE 3

| CALCULATED ANALYSIS OF THE DIETS | | |
|---|---|---|
| Constituent | Starter (%) | Grower (%) |
| Crude protein | 21.0 | 19.0 |
| Total Lysine | 1.20 | 1.00 |
| Total Methionine | 0.52 | 0.46 |
| Tot Meth. + Cyst | 0.88 | 0.80 |
| Calcium | 0.9 | 0.9 |
| Av. Phosphorous | 0.45 | 0.40 |
| ME kcal/kg | 3190 | 3250 |
| MJ/kg | 13.3 | 13.6 |

TABLE 4

| EXPERIMENTAL DESIGN | | | |
|---|---|---|---|
| Treatment | Coccidiostat (ppm) | Betaine (%) | Inoculation |
| 1 | 0 | 0 | Yes |
| 2 | 0 | 0.15 | Yes |
| 3 | Salinomycin (44) | 0 | Yes |
| 4 | Salinomycin (44) | 0.15 | Yes |
| 5 | Salinomycin (66) | 0 | Yes |

TABLE 4-continued

EXPERIMENTAL DESIGN

| Treatment | Coccidiostat (ppm) | Betaine (%) | Inoculation |
|---|---|---|---|
| 6 | Salinomycin (66) | 0.15 | Yes |
| 7 | Salinomycin (66) | 0 | No |

Diets: Corn-soy diet (starter and grower) was formulated to meet or exceed the nutritional requirements set forth in NRC 1984, except for methionine, which was deficient in diets 1, 3 and 4. Diet composition is shown in Table 6 and calculated analysis in Table 7. The diets were supplemented with betaine and a commercial coccidiostat, salinomycin, according to the experimental design (Table 8). Diets were supplied in crumble and pellet form ad libitum. A complete record of feed consumption was maintained.

TABLE 5

RESULTS

| | | | 1–21 d | | | 1–45 d | | | 21 d |
|---|---|---|---|---|---|---|---|---|---|
| Treatment number | Coccidiostat (ppm) | Additive | Body weight (kg) | Feed conversion ratio | Mortality (%) | Body weight (kg) | Feed conversion ratio | Mortality (%) | Lesion score |
| 1 | None | None | 0.580 a | 1.433 a | 16.62 a | 1.948 a | 1.977 a | 19.05 a | 3.63 a |
| 2 | None | Betaine | 0.592 b | 1.397 b | 14.06 a | 1.853 a | 1.954 ab | 19.92 a | 3.47 a |
| 3 | Salinomycin (44) | None | 0.604 c | 1.381 bc | 8.38 b | 1.969 ab | 1.936 abc | 10.57 b | 2.88 b |
| 4 | Salinomycin (44) | Betaine | 0.617 d | 1.346 cde | 4.69 c | 1.982 bc | 1.898 cde | 7.14 c | 2.22 cde |
| 5 | Salinomycin (66) | None | 0.617 d | 1.349 cd | 4.69 c | 1.981 bc | 1.920 bcd | 6.99 c | 2.34 cd |
| 6 | Salinomycin (66) | Betaine | 0.640 f | 1.311 def | 2.70 c | 2.004 cd | 1.877 def | 4.32 c | 1.81 e |
| 7 | Salinomycin (66) (no inoculation) | None | 0.640 f | 1.289 ef | 2.84 c | 2.010 d | 1.833 f | 4.17 c | 2.44 bc |
| ANOVA | | | <0.001 | 0.004 | 0.0065 | 0.1135 | 0.0767 | 0.0088 | 0.0039 |
| Overall Betaine effect | | | *** | ** | ** | NS | NS | ** | *** |
| Betaine × Salinomycin interaction | | | 0.3049 NS | 0.9409 NS | 0.7581 NS | 0.6751 NS | 0.9028 NS | 0.9627 NS | 0.3533 NS | a, b, c, . . . — means with different letters differ significantly at (P < 0.05)

Conclusions

The data show that betaine addition in a commercial-type compound feed significantly reduces the severity of gut lesions and mortality, and improves the growth and feed efficiency of broiler chicks. While betaine and coccidiostat (salinomycin) both produced a significant effect on these parameters, there was no statistically significant interaction between betaine and the coccidiostat. Thus betaine addition resulted in further improvement in these production parameters in broilers treated with the coccidiostat.

Furthermore, the data show that broilers treated with a lower dietary level (44 ppm) of coccidiostat than in commercial practice, and supplemented with betaine at a dietary level of 1.5 kg/metric ton, show similar performance to broilers treated with the commercial (66 ppm) level of the coccidiostat without betaine.

EXAMPLE 2

Animals: One-day-old (1,200 male and 1,200 female) broiler chicks of commercial strain (Peterson x Arbor Acres) were randomly allotted to 40 floor pens on built-up litter. Chicks were grown to 47 days of age on a basal diet containing salinomycin and supplemented with methionine, betaine, or a combination of both. The experimental design is shown in Table 8. Each of the five treatments had eight replicates.

Inoculation: Chicks were inoculated at 15 days of age with a mixture of E. acervulina, E. maxima and E. tenella via drinking water. At 21 days of age, six birds from each pen were necropsied and scored for coccidiosis at four points of the intestinal tract (upper, middle, lower, cecum; scale: 0–4, 4 is most severe).

Figure 5:
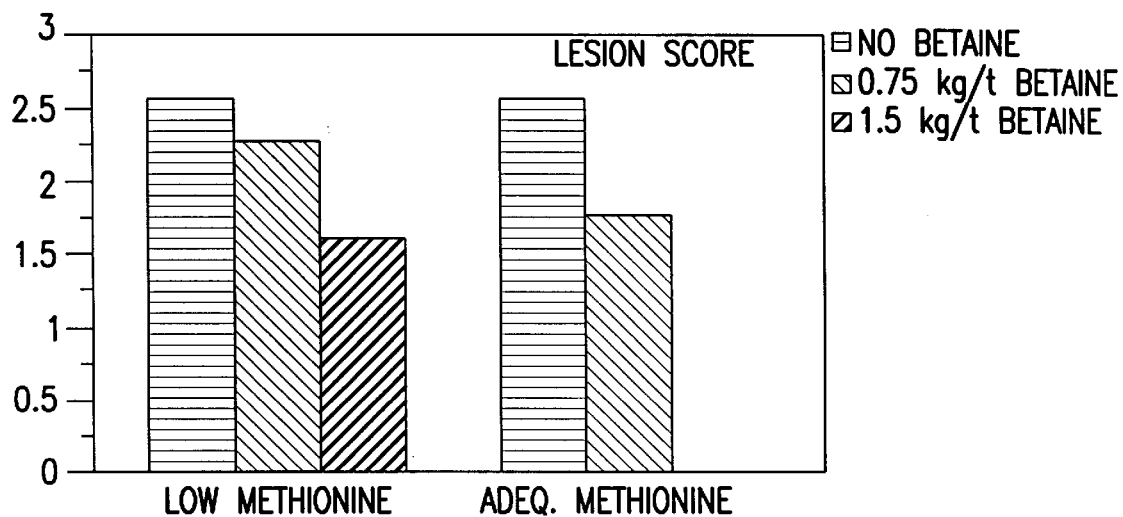
FIG. 5: Coccidia infected chicks were gown on diets containing either adequate methionine or on diets low in methionine was examined. All chicks received 66 ppm of salinomycin. The figure shows that the addition of betaine reduced the severity of gut lesions regardless of the level of methionine.
Figure 6:
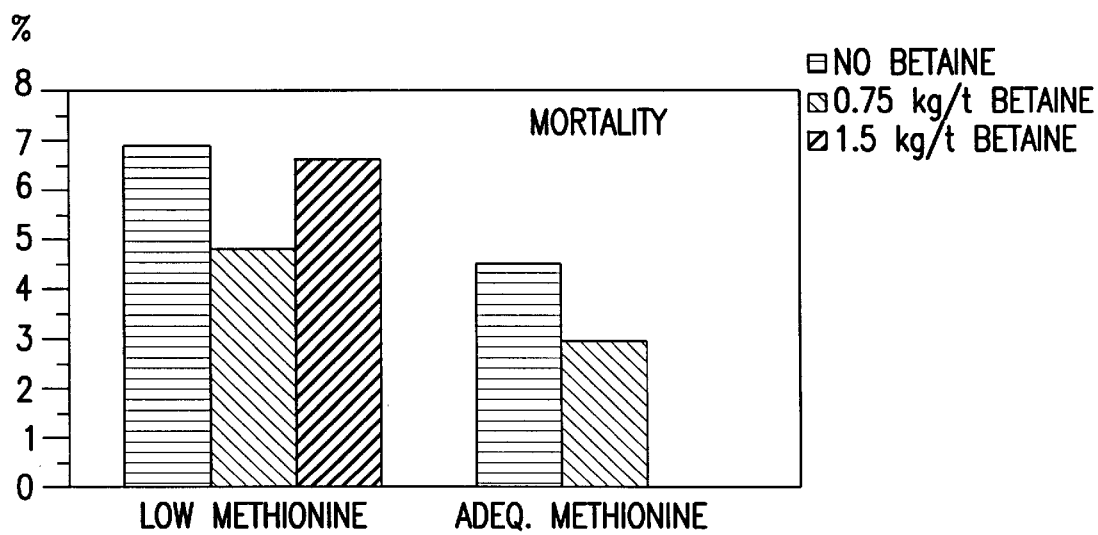
FIG. 6.
Figure 7:
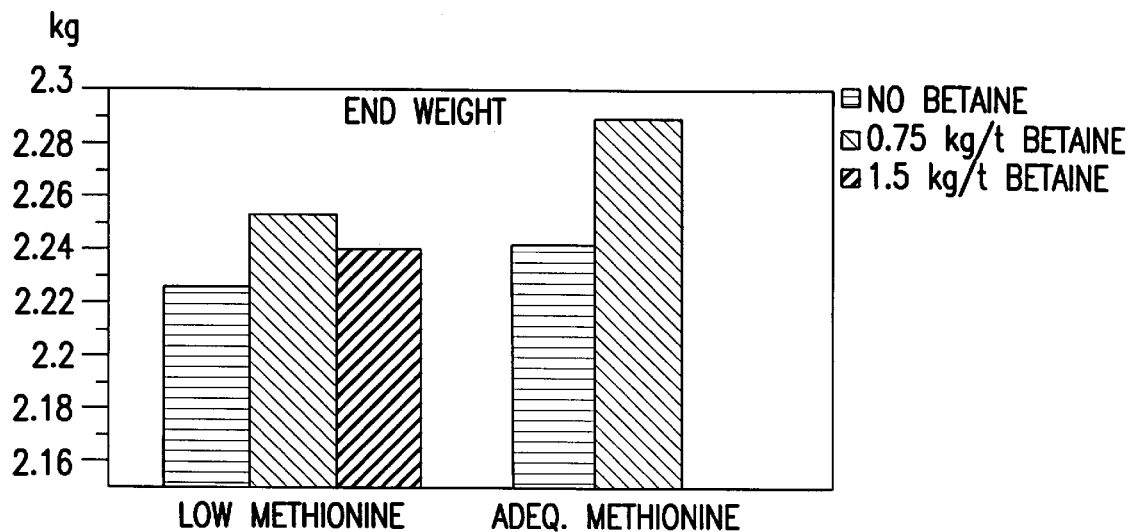
FIG. 7.
Figure 8:
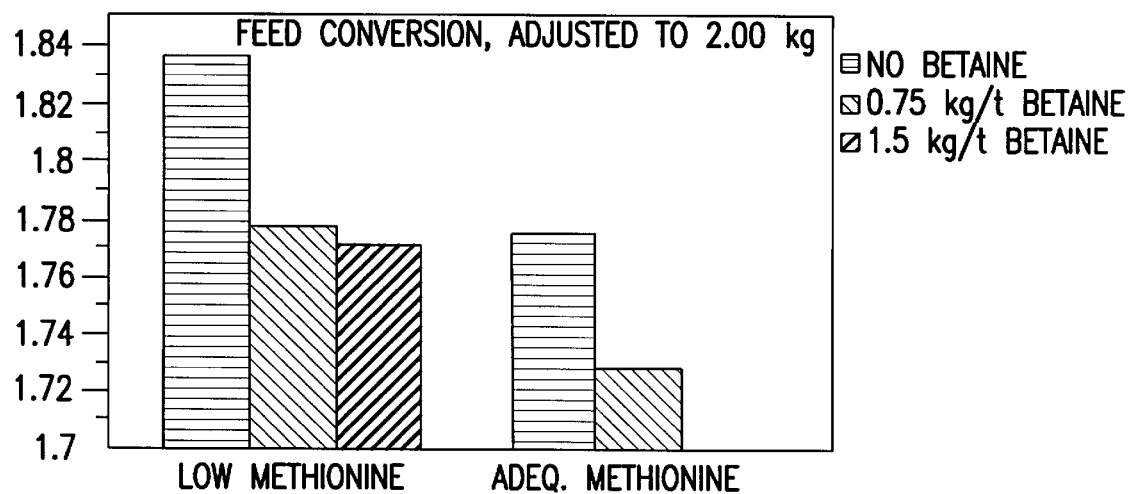
FIG. 8.

The results are disclosed in Table 9 and in FIGS. 5–8. The letters after the numerical data indicate the statistical significance of the differences between the treatments, determined with analysis of variance. Treatments marked with the same letter do not differ significantly as regards the measured parameter.

TABLE 6

DIET COMPOSITION

| Ingredient | Starter (%) | Grower (%) | Finisher (%) |
|---|---|---|---|
| Yellow corn | 57.23 | 62.58 | 68.33 |
| Soybean meal (46.5) | 31.64 | 27.3 | 21.02 |
| Meat and bone meal (48) | 5.00 | 5.00 | 5.00 |
| Fat | 3.89 | 3.97 | 3.90 |
| Salt | 0.33 | 0.34 | 0.36 |
| DL Methionine | 0.024 | 0.041 | 0.00 |
| Limestone | 0.44 | 0.41 | 0.48 |
| Def. phos | 0.66 | 0.54 | 0.30 |
| Trace mineral premix | 0.25 | 0.25 | 0.25 |
| Vitamin premix | 0.05 | 0.05 | 0.05 |
| Bacitracin MD | 0.05 | 0.025 | 0.025 |
| Chlorine chloride-60 | 0.087 | 0.084 | 0.06 |
| 3-nitro-20 | 0.025 | 0.025 | 0.00 |
| Sand, fine washed | 0.225 | 0.225 | 0.225 |

TABLE 7

CALCULATED ANALYSIS OF THE DIETS

| Constituent | Starter (%) | Grower (%) | Finisher (%) |
|---|---|---|---|
| Crude protein % | 22.0 | 20.0 | 18.01 |
| Total Lysine % | 1.164 | 1.024 | 0.883 |
| Total Methionine % | 0.376 | 0.368 | 0.303 |
| Tot Meth. + Cyst % | 0.709 | 0.672 | 0.579 |
| Choline | 0.165 | 0.154 | 0.132 |
| Calcium % | 0.92 | 0.86 | 0.80 |
| Av. Phosphorous % | 0.48 | 0.45 | 0.40 |
| ME kcal/kg | 3100 | 3170 | 3240 |
| MJ/kg | 13.0 | 13.3 | 13.5 |

TABLE 8

EXPERIMENTAL DESIGN

| Treatment | Coccidiostat (ppm) | Added methionine above basal (%) | Betaine (%) | Inoculation |
|---|---|---|---|---|
| 1 | Salinomycin (66) | 0 | 0 | Yes |
| 2 | Salinomycin (66) | 0.15 | 0 | Yes |
| 3 | Salinomycin (66) | 0 | 0.075 | Yes |
| 4 | Salinomycin (66) | 0 | 0.15 | Yes |
| 5 | Salinomycin (66) | 0.15 | 0.075 | Yes |

TABLE 9

RESULTS

|  | Tr. 1 LM, 0 BET | Tr. 2 HM, 0 BET | Tr. 3 LM, 0.75 BET | Tr. 4 LM, 1.5 BET | Tr. 5 HM, 0.75 BET |
|---|---|---|---|---|---|
| End weight, kg | 2.227 a | 2.243 a | 2.253 a | 2.242 a | 2.291 b |
| FCR | 1.928 a | 1.872 b | 1.880 b | 1.869 b | 1.846 c |
| FCR, weight adjusted | 1.837 a | 1.775 b | 1.778 b | 1.772 b | 1.730 c |
| Lesion score | 2.478 a | 2.541 ab | 2.188 ab | 1.563 b | 1.770 ab |
| Mortality % | 6.875 a | 4.583 a | 4.792 a | 6.667 a | 3.125 a |

Explanations:
LM = low (0.37%) methionine,
HM = high = adequate (0.52%) methionine
0 BET = no betaine,
0.75 BET = 0.75 kg/metric ton (1.5 lb/ton) betaine,
1.5 BET = 1.5 kg/metric ton (3 lb/ton) betaine
FCR = feed conversion ratio, mortality adjusted
FCR, weight adjusted = FCR adjusted to 2.0 kg weight, using 0.04 decrease in FCR per 100 g live weight
Lesion score = sum of lesion scores (0 to 4) at four points of the intestine
Common letters after the mean values express non-significant differences between the treatments Conclusions Betaine addition at levels 0.075–0.15 % of the diet significantly improved the growth and feed efficiency of broilers. 0.15% betaine significantly reduced intestinal lesions caused by coccidial infection. The response was not dependent on the methionine content of the diet.

EXAMPLE 3

Animals: 1200 one-day-old male broiler chicks of commercial strain (Peterson x Arbor Acres) were randomly allotted to 120 battery cages of 18"×24". Chicks were grown to 21 days of age. There were ten treatment groups, each with twelve replicates. The experimental design is shown in Table 10.

Inoculation: Chicks in treatments 1, 2 and 5–10 were inoculated at 14 days of age with a mixture of *E. acervulina, E. maxima* and *E. tenella* via drinking water. At 21 days of age, 4 birds from each cage were necropsied and scored for coccidiosis (0–4, 4 is most severe). Treatments 3 and 4 were non-inoculated controls.

Diets: Corn-soy diets were formulated to meet or exceed the nutritional requirements set forth in *Nutrient Requirements of Poultry,* National Research Council, National Academy of Sciences, Washington, D.C. (1984). Diet composition is shown in Table 11 and calculated analysis in Table 12. The diets were supplemented with betaine and three kinds of commercial coccidiostat according to the experimental design (Table 10). A complete record on feed consumption was maintained.

The results are disclosed in the following tables and figures. The letters after the numerical data indicate the statistical significance of the differences between the treatments, determined with analysis of variance. Treatments marked with the same letter do not differ significantly with regard to the measured parameter.

TABLE 10

Experimental Design

| Treatment No. | Added betaine (lb/ton) | Coccidiostat source | Coccidia inoculation |
|---|---|---|---|
| T1 | None | None | Y |
| T2 | Betaine 3 lb/t | None | Y |
| T3 | None | None | N |
| T4 | Betaine 3 lb/t | None | N |
| T5 | None | Salinomycin (60 g/t) | Y |
| T6 | None | Lasalocid (113 g/t) | Y |
| T7 | None | Halofugionone hydrobromide | Y |

TABLE 10-continued

Experimental Design

| Treatment No. | Added betaine (lb/ton) | Coccidiostat source | Coccidia inoculation |
|---|---|---|---|
| | | (2.72 g/t) | |
| T8 | Betaine 3 lb/t | Salinomycin (60 g/t) | Y |
| T9 | Betaine 3 lb/t | Lasalocid (113 g/t) | Y |
| T10 | Betaine 3 lb/t | Halofugionone hydrobromide (2.72 g/t) | Y |

TABLE 11

Diet Composition

| Ingredient | % |
|---|---|
| Yellow corn | 59.174 |
| Soybean Meal (48%) | 32.801 |
| Fat 3700 | 2.379 |
| Salt | 0.199 |
| Limestone | 0.595 |
| Def. Phos. (32-18) | 1.604 |
| Choline (CH-60%) | 0.002 |
| Trace Mineral Premix | 0.050 |
| Vitamin Premix | 0.050 |
| DL Methionine | 0.145 |
| Corn GL (ML-61%) | 3.000 |

TABLE 12

Calculated Analysis of the Diet

| Nutrient | |
|---|---|
| Protein % | 22.82 |
| Energy - kcal/lb | 1,425.00 |
| Lysine % | 1.20 |
| Methionine + Cysteine % | 0.92 |
| Methionine % | 0.54 |
| Available Phosphate % | 0.43 |
| Sodium % | 0.18 |
| Chlorine g/kg | 1.00 |
| Calcium % | 0.85 |
| Xanthophyll | 9.51 |

EXAMPLE 4

The efficacy of betaine in improving growing broiler performance was further examined. To determine if betaine improves performance of growing broilers fed various coccidiostats, broilers were fed feed to which either betaine alone was added, or, betaine was added with a coccidiostat. The coccidiostats examined were salinomycin, monensin, narasin, nicarbazin, diclazuril, robenide hydrochloride, zoalene, and maduramicin ammonium. The health performance (three week lesion scores, mortality, and morbidity) of the broilers reared in battery units was also examined.

Commercial broiler strains supplied by ConAgra Hatchery, Hurlock, Md. (specie: broiler chick; strain: Peterson X Arbor Acres) were used.

All experimental feeds were mixed and provided by PARC Institute, Inc., Queen Anne, Md. A control feed containing all known requirements was formulated by PARC and mixed at one time; a portion ($\frac{1}{20}$) was taken from the control to which all products were added. This procedure assured that all rations contained the same proportion of major ingredients. The diets conformed to industry standards and met or exceeded the nutritional requirements set forth in "Nutrient Requirements of Poultry", 8th rev. ed., National Research Council, 1984. All rations were formulated using commercial standards. Special care was taken to weigh and mix each premix source properly since very small amounts were added. Mixing was performed for 12 minutes. All test materials were stored in cold room storage.

The chicks were used starting at 1 day of age and reared to 21 days (1.4 pounds). Two thousand, four hundred (2,400) male chicks were used.

The chick density in the building was 0.30 ft$^2$. There were 10 birds per cage. All birds were placed in disinfected battery units measuring 18" by 24"; each battery unit consisted of 24 individual cages arranged in six tiers. The temperature was maintained at 85°–90° F.

At 14 days of age, a mixture of E. acervulina (100,000 per bird), E. maxima (50,000 per bird) and E. tenella (10,000 per bird) was administered in the drinking water for the purpose of simulating commercial coccidiosis challenge. The study was terminated on trial day 21 (21 days of age). All birds from each cage (or lot) were necropsied and scored for coccidiosis using the four gut areas (upper small intestine, lower small intestine, large intestine, and cecum) and point

TABLE 13

Results

| Trt. no. | Added betaine (lb/ton) | Coccidiostat source | Coccidia inoculation | 1–21 d Body weight lb | 1–21 d Feed conversion ratio | 1–21 d Mortality % |
|---|---|---|---|---|---|---|
| T1 | None | None | Y | 1.066 e | 1.625 g | 41.6 d |
| T2 | Betaine 3 lb/t | None | Y | 1.228 d | 1.582 f | 32.5 d |
| T3 | None | None | N | 1.434 a | 1.279 a | 5.8 a |
| T4 | Betaine 3 lb/t | None | N | 1.427 ab | 1.275 a | 1.6 a |
| T5 | None | Salinomycin (60 g/t) | Y | 1.238 d | 1.399 e | 15.8 bc |
| T6 | None | Lasalocid (113 g/t) | Y | 1.250 cd | 1.376 de | 17.5 c |
| T7 | None | Halofugionone hydrobromide (2.72 g/t) | Y | 1.357 ab | 1.407 e | 15.8 bc |
| T8 | Betaine 3 lb/t | Salinomycin (60 g/t) | Y | 1.375 ab | 1.344 bc | 5.8 ab |
| T9 | Betaine 3 lb/t | Lasalocid (113 g/t) | Y | 1.335 bc | 1.304 ab | 6.6 abc |
| T10 | Betaine 3 lb/t | Halofugionone hydrobromide (2.72 g/t) | Y | 1.406 ab | 1.348 cd | 5.8 ab | system described in the detailed description of the invention (0–4, where 4 is most severe).

All birds that died during the experiment were necropsied to determine the cause of death. Birds were culled if they could not get to the food and water. Experimental broiler feed was formulated to meet the nutrient requirements set forth by the NRC (National Research Council), 1984. The feed was fed in crumbled form from day 1 to day 21 (test period).

Statistical significance at the 5% level of probability was determined using ANOVA analysis and least significance differences to separate significance.

TABLE 14

Study Design

| Treatment ID# | Coccidiostat | Inoculated Yes or No | Added betaine Yes or No |
|---|---|---|---|
| F1 | none | no | no |
| F2 | none | no | yes: 3 pounds/ton |
| F3 | none | yes | no |
| F4 | none | yes | yes: 3 pounds/ton |
| F5 | salinomycin | yes | yes: 3 pounds/ton |
| F6 | salinomycin | yes | no |
| F7 | monensin | yes | yes: 3 pounds/ton |
| F8 | monensin | yes | no |
| F9 | narasin | yes | yes: 3 pounds/ton |
| F10 | narasin | yes | no |
| F11 | nicarbazin | yes | yes: 3 pounds/ton |
| F12 | nicarbazin | yes | no |
| F13 | diclazuril | yes | yes: 3 pounds/ton |
| F14 | diclazuril | yes | no |
| F15 | robenide HCl | yes | yes: 3 pounds/ton |
| F16 | robenide HCl | yes | no |
| F17 | zoalene | yes | yes: 3 pounds/ton |
| F18 | zoalene | yes | no |
| F19 | maduramicin ammonium | yes | yes: 3 pounds/ton |
| F20 | maduramicin ammonium | yes | no |

The basal ration was formulated to isocaloric and isonitrogenous conditions. The feed formula used in this study was as follows:

| | |
|---|---|
| 60.05% | yellow corn; |
| 32.62% | 48% soybean meal (48% crude protein); |
| 4.35% | fat 3700; |
| 0.20% | salt; |
| 0.58% | limestone; |
| 1.63% | Def. phos. 32-18 (32% calcium; 18% phosphate); |
| 0.25% | 70% choline chloride; |
| 0.05% | trace mineral premix; |
| 0.05% | vitamin premix; and |
| 0.22% | DL-methionine. |

The nutrient composition of this diets was as follows:

| | |
|---|---|
| 21.50% | protein; |
| 1,425.00 | kcal/lb; |
| 1.20% | lysine; |
| 0.92% | methionine + cysteine; |
| 0.56% | methionine; |
| 0.43% | available phosphate; |
| 0.18% | sodium; |
| 2.5 g/kg | choline; |
| 0.85% | calcium; and |
| 6.8% | fat. |

Each ration was fed to 12 lots of 10 broilers per lot. The results are shown below.

TABLE 15

Body Weight (pounds)

| | | Betaine level (pound per ton) | | |
|---|---|---|---|---|
| Coccidiostat | Inoculation | none | 3.00 | Mean* |
| Control | no | 1.389 ABCD | 1.392 ABC | |
| Control | yes | 1.305 G | 1.301 G | |
| Salinomycin | yes | 1.344 F | 1.386 A–E | 1.365 b |
| Monensin | yes | 1.365 CDEF | 1.387 A–E | 1.376 ab |
| Narasin | yes | 1.355 EF | 1.388 ABCD | 1.372 b |
| Nicarbazin | yes | 1.402 A | 1.389 ABCD | 1.395 a |
| Diclazuril | yes | 1.358 DEF | 1.389 ABCD | 1.374 b |
| Robenide hydrochloride | yes | 1.398 AB | 1.395 ABC | 1.397 a |
| Zoalene | yes | 1.352 F | 1.406 A | 1.379 ab |
| Maduramicin ammonium | yes | 1.367 B–F | 1.385 A–E | 1.376 ab |
| Mean* | | 1.363 b | 1.382 a | |

*Mean refers to Main Effects only. Main Effect means within either a column or row are significantly different (P < 0.05) if followed by a different small letter as determined by least significant difference analysis.
"Treatment means" are shown by the large letters that follow the number.

TABLE 16

Feed Conversion Ratio

| | | Betaine level (pound per ton) | | |
|---|---|---|---|---|
| Coccidiostat | Inoculation | none | 3.00 | Mean* |
| Control | no | 1.339 H | 1.349 GH | |
| Control | yes | 1.456 A | 1.458 A | |
| Salinomycin | yes | 1.411 BC | 1.376 EF | 1.393 bc |
| Monensin | yes | 1.423 B | 1.381 DEF | 1.402 bc |
| Narasin | yes | 1.409 BC | 1.368 FG | 1.388 b |
| Nicarbazin | yes | 1.350 GH | 1.359 FGH | 1.354 a |
| Diclazuril | yes | 1.407 BC | 1.369 EFG | 1.388 b |
| Robenide hydrochloride | yes | 1.363 FGH | 1.359 FGH | 1.361 a |
| Zoalene | yes | 1.423 B | 1.394 CDE | 1.409 c |
| Maduramicin ammonium | yes | 1.406 BCD | 1.370 EFG | 1.388 b |
| Mean* | | 1.399 b | 1.378 a | |

*Mean refers to Main Effects only. Main Effect means within either a column or row are significantly different (P < 0.05) if followed by a different small letter as determined by least significant difference analysis.
"Treatment means" are shown by the large letters that follow the number.

TABLE 17

Mortality (%)

| | | Betaine level (pound per ton) | | |
|---|---|---|---|---|
| Coccidiostat | Inoculation | none | 3.00 | Mean* |
| Control | no | 3.33 F | 4.17 EF | |
| Control | yes | 34.17 A | 32.50 A | |
| Salinomycin | yes | 10.83 BCD | 5.83 CDEF | 8.33 bc |
| Monensin | yes | 13.33 B | 5.83 CDEF | 9.58 c |
| Narasin | yes | 12.50 B | 5.00 DEF | 8.75 bc |
| Nicarbazin | yes | 5.00 DEF | 5.00 DEF | 5.00 ab |
| Diclazuril | yes | 10.00 BCDE | 5.83 CDEF | 7.92 abc |
| Robenide hydrochloride | yes | 3.33 F | 4.17 EF | 3.75 a |
| Zoalene | yes | 11.67 BC | 5.83 CDEF | 8.75 bc |

TABLE 17-continued

Mortality (%)

Betaine level (pound per ton)

| Coccidiostat | Inoculation | none | 3.00 | Mean* |
|---|---|---|---|---|
| Madurami-cin ammonium | yes | 12.50 B | 5.00 DEF | 8.75 bc |
| Mean* | | 11.67 b | 7.92 a | |

*Mean refers to Main Effects only. Main Effect means within either a column or row are significantly different (P < 0.05) if followed by a different small letter as determined by least significant difference analysis.
"Treatment means" are shown by the large letters that follow the number.

TABLE 18

Total Lesion Score

Betaine level (pound per ton)

| Coccidiostat | Inoculation | none | 3.00 | Mean* |
|---|---|---|---|---|
| Control | no | 0.08 J | 0.13 IJ | |
| Control | yes | 5.88 A | 5.75 A | |
| Salinomycin | yes | 1.81 CDE | 0.81 FGHI | 1.31 b |
| Monensin | yes | 2.46 BC | 1.48 DEF | 1.97 c |
| Narasin | yes | 2.15 BCD | 1.00 FGH | 1.57 bc |
| Nicarbazin | yes | 0.69 GHIJ | 0.54 HIJ | 0.61 a |
| Diclazuril | yes | 2.00 BCDE | 0.94 FGH | 1.47 bc |
| Robenide hydrochlor-ide | yes | 0.63 GHIJ | 0.44 HIJ | 0.53 a |
| Zoalene | yes | 2.71 B | 1.29 EFG | 2.00 c |
| Madurami-cin ammonium | yes | 2.38 BC | 0.67 GHIJ | 1.52 bc |
| Mean* | | 2.08 b | 1.30 a | |

*Mean refers to Main Effects only. Main Effect means within either a column or row are significantly different (P < 0.05) if followed by a different small letter as determined by least significant difference analysis.
"Treatment means" are shown by the large letters that follow the number.

The data demonstrate that betaine positively affected lesion score, mortality, growth and feed conversion ratio when used in combination with coccidiostats.

EXAMPLE 5

Co-administration of Betaine and Coccidiostat in Other Species

Co-administration of betaine and coccidiostats are used as herein, but are administered to cattle, rabbits, goats, swine, sheep, dogs, cats, birds, fish, geese, guinea fowl, pigeons, ducks, quail, or turkeys.

EXAMPLE 6

Effect of Betaine on Vaccinated Chicks

Betaine (from 0.5 to 1.5 kilograms (kg) per metric ton of dry feed—equivalent to 1–3 pounds per ton) was added into the diet of chickens vaccinated against *Eimeria tenella, E. mivati, E. maxima* and *E. acervulina* using the vaccine tradenamed "Coccivac-B™" (produced by Sterwin Laboratories) during the first 35 days of the animal's life, or, during the whole 56 day growing period. The vaccine was given on day 1 as recommended by the manufacturer. The betaine-containing diet also started on day 1. Performance evaluations were evaluated as above. The treatments were as follows:

Treatment 1: vaccinated birds fed a low-methionine diet, no betaine.

Treatment 2: vaccinated birds fed a low-methionine diet, supplemented with betaine (1 lb /(short) ton=0.5 kg/metric ton).

Treatment 3: vaccinated birds fed an adequate methionine diet, no betaine.

Treatment 4: vaccinated birds fed an adequate methionine diet, supplemented with betaine (3 lb/ (short) ton=1.5 kg/metric ton).

Treatment 5: vaccinated birds fed an adequate methionine diet, supplemented during the first 35 days with with betaine (3 lb/ (short) ton=1.5 kg/metric ton).

Treatment 6: Non-vaccinated birds fed an adequate-methionine diet with salinomycin coccidiostat, no betaine.

Treatments 1, 2, 4 and 5 tested whether betaine at different doses and times of treatment affected the lesion score and bird performance. Treatments 1, 2 and 3 tested whether dietary methionine affected the lesion score and bird performance. Lastly, the treatments tested how vaccinated birds supplemented with betaine perform as compared with birds with a coccidiostat (exemplified using salinomycin).

The results demonstrated that when betaine was added into the diet of the vaccinated chickens, the chickens grew and utilized their feed equally to or better than non-vaccinated chickens that were fed a diet with a common coccidiostat (salinomycin).

Addition of betaine reduced the severity of gut lesions, independently of the methionine level of the diet. Significant differences between vaccinated animals whose diets were supplemented betaine and those whose diets were not supplemented were found 22 days after hatching. Significant treatment effects were found.

For vaccinated males, carcass evaluation including live weight, hot weight, chill weight, breast weight and percent breast were significantly better for betaine treated males than for untreated males. There was no significant treatment effects for vaccinated females on the carcass evaluation.

Betaine treated vaccinated males and females showed a significant improvement in carcass quality.

The study demonstrates that betaine alleviated the adverse effects of vaccination, resulting in good performance in broilers grown to normal 6–7 weeks of age. Hence, the application area for vaccines against coccidiosis can be markedly increased.

EXAMPLE 7

Betaine Administration to Vaccinated Animals

Geese, guinea fowl, pigeons, ducks, quail, turkeys, cattle, rabbits, goats, swine or sheep are vaccinated as described herein, and administered an betaine-containing diet that contains an efficacious amount betaine at a concentration of between 0.1 kg/metric ton–5 kg/metric ton dry weight, or at the concentration of 0.01 to 0.5 g per kg body weight of the animal or at the concentration of 0.03 to 3.0 kg per metric ton of drinking water. The animals are fed this diet continuously after vaccination, for a time sufficient to extend beyond the period during which the vaccine-induced coccidiosis infection would have occurred.

What is claimed is:

1. A method for treating an animal for subclinical or clinical coccidiosis, said method comprising administering betaine to said animal at amounts efficacious for the treatment of said coccidiosis.

2. The method of claim 1, wherein said betaine is administered at the concentration of 0.01 to 0.5 g per kg body weight of the animal.

3. The method of claim 1, wherein said betaine is administered at the concentration of 0.1 to 5.0 kg per kg metric ton of feed.

4. The method of claim 1, wherein said betaine is administered at the concentration of 0.03 to 3.0 kg per metric ton of drinking water.

5. The method of claim 1, wherein said coccidiosis is due to a member to the Eimeria species.

6. The method of claim 5, wherein said member of said Eimeria species is selected from the group consisting of acervulina, ahsata, arloingi A (ovina), bows (smithii), brunetti, caprovina, christenseni crandallis, debliecki, dispersa, ellipsoidlis, faurel, galloparvonis, gilruthi, innocua, maxima, meleagridis, meleagrimitis, mitis, necatrix, ninakohlyakimovae, ovinoidalis, perminuta, praecox, scabra, subrotunda, tenella, truncata, weybridgensis (arlongis B), and zuernii.

7. The method of claim 6, wherein said Eimeria species is selected from the group consisting of acervulina, brunetti, dispersa, galloparvonis, innocua, maxima, meleagridis, meleagrimitis, mitis, necatrix, praecox, subrotunda, tenella, and truncata.

8. The method of any one of claims 1 or 2–7, wherein said coccidiosis is the result of a vaccination of said animal with a coccidiosis vaccine.

9. The method of claim 1, wherein said animal is selected from the group consisting of poultry, cattle, rabbits, goats, swine, sheep, dogs, cats, birds and fish.

10. The method of claim 9, wherein said poultry animal is selected from the group consisting of chickens, ducks and turkeys.

11. The method of any one of claims 1 or 2–7, wherein said coccidiosis is the result of an environmental infection.

12. The method of claim 11, wherein said method further comprises the administration of a coccidiostat to said animal.

13. The method of claim 12, wherein said coccidiostat is an ionophore coccidiostat.

14. The method of claim 13, wherein said ionophore coccidiostat is selected from the group consisting of: maduramicin ammonium, lasalocid, monensin, narasin, and salinomycin.

15. The method of claim 14, wherein said ionophore coccidiostat is salinomycin.

16. The method of claim 12, wherein said coccidiostat is a chemical coccidiostat.

17. The method of claim 16, wherein said chemical coccidiostat is selected from the group consisting of: amprolium, clopidol, decoquinate, diclazuril, halofuginone hydrobromide, nicarbazin, robenide hydrochloride, and zoalene.

18. The method of claim 17, wherein said chemical coccidiostat is halofuginone hydrobromide.

* * * * *